US011385146B2

(12) United States Patent
Harding et al.

(10) Patent No.: US 11,385,146 B2
(45) Date of Patent: Jul. 12, 2022

(54) SAMPLING SYSTEMS AND TECHNIQUES TO COLLECT HAZARDOUS CONTAMINANTS WITH HIGH PICKUP AND SHEDDING EFFICIENCIES

(71) Applicant: Becton, Dickinson and Company, Franklin Lakes, NJ (US)

(72) Inventors: Weston F. Harding, Lehi, UT (US); Austin Jason Mckinnon, Herriman, UT (US); Matthew Oshinski, Oak Ridge, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 731 days.

(21) Appl. No.: 16/134,105

(22) Filed: Sep. 18, 2018

(65) Prior Publication Data

US 2019/0086305 A1    Mar. 21, 2019

Related U.S. Application Data

(60) Provisional application No. 62/561,552, filed on Sep. 21, 2017.

(51) Int. Cl.
  *G01N 1/40* (2006.01)
  *G01N 1/02* (2006.01)
  (Continued)

(52) U.S. Cl.
  CPC ............ *G01N 1/405* (2013.01); *B01L 3/5029* (2013.01); *G01N 1/02* (2013.01); *G01N 33/15* (2013.01);
  (Continued)

(58) Field of Classification Search
  None
  See application file for complete search history.

(56) References Cited

U.S. PATENT DOCUMENTS

| 1,853,238 A | 4/1932 | Shields |
| D229,689 S | 12/1973 | Dragotta |

(Continued)

FOREIGN PATENT DOCUMENTS

| CN | 107102103 A | 8/2017 |
| WO | WO 1995/25948 | 9/1995 |

(Continued)

OTHER PUBLICATIONS

Becton Dickinson—BD HD Check Analyzer—Nursing Brochure; Mar. 2018, in 8 pages.

(Continued)

*Primary Examiner* — Lore R Jarrett
(74) *Attorney, Agent, or Firm* — Knobbe, Martens, Olson & Bear, LLP

(57) ABSTRACT

Sampling systems and techniques that increase pickup efficiency and shedding efficiency of an analyst of interest collected from a surface are provided. In one aspect, an absorbent swab collects an analyte of interest, such as a hazardous contaminant, from a test area demarcated by a template. The sampling techniques can include swab speed and force protocols specifying how fast and how hard the user should apply the swab across the surface to improve pickup efficiency. The sampling techniques can include instructions for inverting a container enclosing the swab and collected contaminant to improve shedding efficiency from the swab.

21 Claims, 15 Drawing Sheets

(51) Int. Cl.
  *G01N 33/15* (2006.01)
  *B01L 3/00* (2006.01)
  *G01N 1/38* (2006.01)

(52) U.S. Cl.
  CPC ......... *B01L 3/5082* (2013.01); *B01L 3/50825* (2013.01); *B01L 2200/082* (2013.01); *B01L 2200/16* (2013.01); *B01L 2200/185* (2013.01); *B01L 2300/0825* (2013.01); *G01N 1/38* (2013.01); *G01N 2001/028* (2013.01)

(56) References Cited

U.S. PATENT DOCUMENTS

| | | | |
|---|---|---|---|
| 3,841,973 A | 10/1974 | Wilkins et al. | |
| 4,278,437 A | 7/1981 | Haggar | |
| 4,353,868 A | 10/1982 | Joslin et al. | |
| 4,707,450 A | 11/1987 | Nason | |
| 4,724,307 A | 2/1988 | Dutton et al. | |
| 4,956,302 A | 9/1990 | Gordon et al. | |
| 5,243,865 A | 9/1993 | Hsu et al. | |
| 5,373,748 A | 12/1994 | Lioy et al. | |
| 5,422,273 A | 6/1995 | Garrison et al. | |
| 5,511,654 A | 4/1996 | de la Rocha | |
| 5,511,934 A | 4/1996 | Bracchi et al. | |
| 5,543,115 A | 8/1996 | Karakawa | |
| D383,851 S | 9/1997 | Wong | |
| 5,798,273 A | 8/1998 | Shuler et al. | |
| 5,823,592 A | 10/1998 | Kalidindi et al. | |
| 5,888,758 A | 3/1999 | Wu et al. | |
| D425,625 S | 5/2000 | Niermann | |
| D438,979 S | 2/2001 | Gomes et al. | |
| 6,382,036 B1 | 5/2002 | Woodmansee | |
| 6,541,269 B1* | 4/2003 | Ramana ................ | G01N 21/78 422/401 |
| 6,723,290 B1* | 4/2004 | Wardlaw .......... | G01N 35/00029 422/559 |
| 6,924,153 B1 | 8/2005 | Boehringer et al. | |
| D520,643 S | 5/2006 | Clarke et al. | |
| 7,114,403 B2 | 10/2006 | Wu et al. | |
| D558,357 S | 12/2007 | Byrd et al. | |
| D559,397 S | 1/2008 | Eriksson et al. | |
| D560,281 S | 1/2008 | Kozak et al. | |
| D574,507 S | 8/2008 | Muir et al. | |
| D594,131 S | 6/2009 | Nguyen | |
| 7,837,939 B2 | 11/2010 | Tung et al. | |
| D640,795 S | 6/2011 | Jackson et al. | |
| 8,128,871 B2 | 3/2012 | Petruno et al. | |
| 8,486,717 B2 | 7/2013 | O'Farrell et al. | |
| 8,828,653 B2* | 9/2014 | Zook ....................... | G01N 1/02 435/243 |
| D743,046 S | 11/2015 | Poll et al. | |
| D743,571 S | 11/2015 | Jackson et al. | |
| 9,488,585 B2 | 11/2016 | Emeric et al. | |
| 9,857,372 B1 | 1/2018 | Pulitzer et al. | |
| D859,683 S | 9/2019 | Harding et al. | |
| D882,817 S | 4/2020 | Norton et al. | |
| D898,220 S | 10/2020 | Esala et al. | |
| 10,916,058 B2 | 2/2021 | Isaacson et al. | |
| 11,002,642 B2 | 5/2021 | Oshinski et al. | |
| D923,195 S | 6/2021 | Harding et al. | |
| 2002/0001539 A1 | 1/2002 | Dicesare et al. | |
| 2002/0035869 A1 | 3/2002 | Schroder et al. | |
| 2003/0086074 A1 | 5/2003 | Braig et al. | |
| 2004/0018634 A1 | 1/2004 | Hajizadeh et al. | |
| 2004/0248106 A1 | 12/2004 | Leonard et al. | |
| 2005/0084842 A1 | 4/2005 | O'Connor | |
| 2005/0106753 A1 | 5/2005 | Wu et al. | |
| 2005/0136540 A1 | 6/2005 | Quine et al. | |
| 2005/0136553 A1 | 6/2005 | Kaylor et al. | |
| 2005/0181517 A1 | 8/2005 | Chandler et al. | |
| 2005/0250141 A1 | 11/2005 | Lambert et al. | |
| 2006/0115805 A1 | 6/2006 | Hansen et al. | |
| 2006/0216196 A1 | 9/2006 | Satoh et al. | |
| 2007/0137319 A1* | 6/2007 | Nacson ................... | G01N 1/02 73/864 |
| 2007/0244368 A1 | 10/2007 | Bayliff et al. | |
| 2007/0276786 A1 | 11/2007 | Piedmonte | |
| 2008/0118397 A1 | 5/2008 | Slowey et al. | |
| 2009/0015273 A1 | 1/2009 | Gossen et al. | |
| 2009/0061534 A1 | 3/2009 | Sharrock | |
| 2009/0223635 A1 | 9/2009 | Lawless | |
| 2010/0077843 A1 | 4/2010 | Doraisamy et al. | |
| 2011/0117025 A1 | 5/2011 | Dacosta et al. | |
| 2011/0201099 A1 | 8/2011 | Anderson et al. | |
| 2012/0011944 A1* | 1/2012 | Maughan ................ | A61B 10/02 73/864.34 |
| 2012/0044264 A1 | 2/2012 | Lee et al. | |
| 2012/0107956 A1 | 5/2012 | Boehringer et al. | |
| 2012/0264229 A1 | 10/2012 | Wan | |
| 2012/0282154 A1 | 11/2012 | Slowey et al. | |
| 2013/0203627 A1* | 8/2013 | Moll ................ | G01N 33/54373 506/18 |
| 2013/0253295 A1 | 9/2013 | Tolosa et al. | |
| 2013/0280143 A1 | 10/2013 | Zucchelli et al. | |
| 2014/0017812 A1 | 1/2014 | Smith et al. | |
| 2014/0080129 A1 | 3/2014 | Klunder et al. | |
| 2014/0121487 A1 | 5/2014 | Faybishenko et al. | |
| 2014/0176603 A1 | 6/2014 | Kumar et al. | |
| 2014/0183256 A1 | 7/2014 | Calio et al. | |
| 2014/0210857 A1 | 7/2014 | Liu et al. | |
| 2014/0309556 A1 | 10/2014 | Fletcher et al. | |
| 2015/0132795 A1 | 5/2015 | Griswold et al. | |
| 2015/0211987 A1 | 7/2015 | Burg et al. | |
| 2015/0241358 A1 | 8/2015 | Burg et al. | |
| 2015/0302662 A1 | 10/2015 | Miller | |
| 2016/0019716 A1 | 1/2016 | Huang et al. | |
| 2016/0041167 A1* | 2/2016 | Campbell ............... | A61P 31/12 536/17.6 |
| 2016/0057413 A1 | 2/2016 | Zhou et al. | |
| 2016/0077013 A1 | 3/2016 | Attar et al. | |
| 2016/0078680 A1 | 3/2016 | Reif et al. | |
| 2016/0258874 A1 | 9/2016 | Truex | |
| 2017/0016045 A1 | 1/2017 | McDaniel | |
| 2017/0072393 A1 | 3/2017 | Jackson et al. | |
| 2017/0153185 A1 | 6/2017 | Kisner et al. | |
| 2017/0154438 A1 | 6/2017 | Kisner et al. | |
| 2018/0247024 A1 | 8/2018 | Divine et al. | |
| 2018/0293350 A1 | 10/2018 | Dimov et al. | |
| 2018/0372595 A1 | 12/2018 | Pais et al. | |
| 2019/0035153 A1 | 1/2019 | Dange | |
| 2019/0086295 A1 | 3/2019 | Oshinski et al. | |
| 2019/0086296 A1 | 3/2019 | West | |
| 2019/0086380 A1 | 3/2019 | Harding et al. | |
| 2019/0086431 A1 | 3/2019 | Isaacson et al. | |
| 2019/0088026 A1 | 3/2019 | Isaacson et al. | |
| 2019/0120727 A1 | 4/2019 | Harding et al. | |
| 2020/0241020 A1 | 7/2020 | Oshinski | |
| 2020/0298240 A1 | 9/2020 | Oshinski et al. | |
| 2021/0192850 A1 | 6/2021 | Isaacson et al. | |
| 2021/0255066 A1 | 8/2021 | Oshinski et al. | |

FOREIGN PATENT DOCUMENTS

| | | |
|---|---|---|
| WO | WO 2009/018473 | 2/2009 |
| WO | WO 2010/001296 | 1/2010 |
| WO | WO 2011/095599 | 8/2011 |
| WO | WO 2013/036913 | 3/2013 |
| WO | WO 2014/015076 | 1/2014 |
| WO | WO 2014/025415 | 2/2014 |
| WO | WO 2015/187335 | 12/2015 |
| WO | WO 2016/040642 | 3/2016 |
| WO | WO 2016/078919 | 5/2016 |
| WO | WO 2016/090176 | 6/2016 |

OTHER PUBLICATIONS

Becton Dickinson—BD HD Check Analyzer—Pharmacy Brochure; Mar. 2018, in 6 pages.

Chemoglo, LLC, "ChemoGlo™—Detecting and Removing Hazardous Drugs"; available for download at https://web.archive.org/web/20150801115335/http://chemoglo.com/ at least as early as Aug. 1, 2015; 1 page.

(56) References Cited

OTHER PUBLICATIONS

Chemoglo, LLC, ChemoGlo™ User Manual; available for download at https://web.archive.org/web/20150801115335/http://chemoglo.com/ at least as early as Aug. 1, 2015; 11 pages.

Becton Dickinson—BD Diagnostics Preanalytical Systems—Product Catalogue 2014-15; 2013, Retrieved from internet: <URL:https://www.bd.com/be/dutch/pdfs/PAS_BNL_Prod_Cat_2014_2015_LR_Full_Catalogue.pdf> in 31 pages.

Becton Dickinson Veritor™ System—For Rapid Detection of Respiratory Syncytial Virus (RSV), Aug. 2017, Retrieved from the internet: <URL: https://www.bd.com/en-us/offerings/capabilities/microbiology-solutions/point-of-care-testing/veritor-system> in 16 pages.

Preprocess, Inc., Sampling and Analytical Technique Considerations for Microbial Surface Swab Testing. 2015; Retrieved from the internet: <URL:http://www.preprocessinc.com/files/documents/d5840edf837f077be7b12e53494ed5b8.pdf> in 3 pages.

Technical Service Consultants Ltd., TS/15-T Product Specification Sheet; Issue #5 of Jun. 6, 2016; Retrieved from the Internet: URL: <http://www.tscswabs.co.uk/uploads/images/product-pdfs/product_specification/spec_TS15-T.pdf> in 20 pages.

International Search Report and Written Opinion dated Nov. 15, 2018 for Int'l Application No. PCT/US2018/051427.

De Keuckelaere et al., "Semi-Direct Lysis of Swabs and Evaluation of Their Efficiencies to Recover Human Noroviruses GI and GII from Surfaces", Food Environ Virol. (Jun. 2014) 6:132-139.

Henderson S.J., "Augmented Reality Interfaces for Procedural Tasks", Doctoral Thesis; Columbia University, Apr. 14, 2011, 82 pages.

National Infection Service (England), Detection and enumeration of bacteria in swabs and other environmental samples. National Infection Service Food Water and Environmental Microbiology Standard Method, Sep. 1, 2017; 22 pages.

\* cited by examiner

SAMPLING SYSTEMS AND TECHNIQUES TO COLLECT HAZARDOUS CONTAMINANTS WITH HIGH PICKUP AND SHEDDING EFFICIENCIES

CROSS-REFERENCE TO RELATED APPLICATIONS

This application claims the benefit of U.S. Provisional Patent Application No. 62/561,552, filed on Sep. 21, 2017, entitled "SAMPLING SYSTEMS AND TECHNIQUES TO COLLECT HAZARDOUS CONTAMINANTS WITH HIGH PICKUP AND SHEDDING EFFICIENCIES," the contents of which are hereby incorporated by reference herein.

TECHNICAL FIELD

Systems and methods disclosed herein are directed to environmental contaminant testing, and, more particularly, to techniques that improve pickup or shedding efficiency during sampling of a test area.

BACKGROUND

Antineoplastic drugs are used to treat cancer, and are most often found in a small molecule (like fluoruracil) or antibody format (like Rituximab). Detection of antineoplastic drugs is critical for determining if there is contamination or leakage where the drugs are used and/or dispensed, such as hospital and pharmacy areas.

The nature of antineoplastic drugs make them harmful to healthy cells and tissues as well as the cancerous cells. Precautions should be taken to eliminate or reduce occupational exposure to antineoplastic drugs for healthcare workers. Pharmacists who prepare these drugs and nurses who may prepare and administer them are the two occupational groups who have the highest potential exposure to antineoplastic agents. Additionally, physicians and operating room personnel may also be exposed through the treatment of patients, as patients treated with antineoplastic drugs can excrete these drugs. Hospital staff, such as shipping and receiving personnel, custodial workers, laundry workers and waste handlers, all have the potential to be exposed to these drugs during the course of their work. The increased use of antineoplastic agents in veterinary oncology also puts these workers at risk for exposure to these drugs.

SUMMARY

Antineoplastic drugs are antiproliferative. In some cases they affect the process of cell division by damaging DNA and initiating apoptosis, a form of programmed cell death. While this can be desirable for preventing development and spread of neoplastic (e.g., cancerous) cells, antineoplastic drugs can also affect rapidly dividing non-cancerous cells. As such, antineoplastic drugs can suppress healthy biological functions including bone marrow growth, healing, hair growth, and fertility, to name a few examples.

Studies have associated workplace exposures to antineoplastic drugs with health effects such as skin rashes, hair loss, infertility (temporary and permanent), effects on reproduction and the developing fetus in pregnant women, increased genotoxic effects (e.g., destructive effects on genetic material that can cause mutations), hearing impairment and cancer. These health risks are influenced by the extent of the exposure and the potency and toxicity of the hazardous drug. Although the potential therapeutic benefits of hazardous drugs may outweigh the risks of such side effects for ill patients, exposed health care workers risk these same side effects with no therapeutic benefit. Further, it is known that exposures to even very small concentrations of antineoplastic drugs may be hazardous for workers who handle them or work near them, and for known carcinogenic agents there is no safe level of exposure.

Environmental sampling can be used to determine the level of workplace contamination by antineoplastic agents. Sampling and decontamination of contaminated areas is complicated, however, by a lack of quick, inexpensive methods to first identify these areas and then determine the level of success of the decontamination. Although analytical methods are available for testing for the presence of antineoplastic drugs in environmental samples, these methods require shipment to outside labs, delaying the receipt of sampling results.

In one example sampling system suitable for use with the devices of the present disclosure, work surfaces can be tested for the presence of antineoplastic agents in an environment. Results of the test can be provided very quickly, at the site of testing, so that the operator of the test, other personnel in the area, and/or remote systems can be alerted to the presence and/or concentration of antineoplastic agents very close in time to the test event, in some cases within 1-2 minutes. Methods of testing include providing the surface with a buffer solution and wiping the wetted surface with an absorbent swab, or by wiping the surface with a swab pre-wetted with the buffer solution. The buffer fluid can have properties that assist in picking up contaminants from the surface. In some implementations, the buffer fluid can have properties that assist in releasing collected contaminants from swab material. The collected contaminants can be mixed into a homogeneous solution for testing. The buffer solution, together with any collected contaminants, can be expressed or extracted from the swab to form a liquid sample. This liquid sample can be analyzed for presence and/or quantity of specific antineoplastic agents. For example, the solution can be provided onto an assay (such as but not limited to a lateral flow assay) which is read by an assay reader device to identify presence and/or a concentration of the contaminant in the liquid sample.

The accuracy of testing for the presence and/or concentration of a contaminant in a fluid sample is highly dependent on various test factors. Test results can provide a measurement in the form of concentration of contaminant in a tested environment, for example contaminant mass per square unit area. Accordingly, precision during sampling can be an important factor to obtain an accurate test result. Determining a concentration of a target hazardous drug can involve a number of different variables relating to the sampling procedure including contamination surface density, area of the test surface swabbed, pickup efficiency (e.g., how much of the actual contamination is picked up by the collection swab), shedding efficiency (e.g., how much of the picked up contamination is extracted from the collection swab), and the volume of buffer solution used during sampling. Excessive noise or variation in these variables will cause a test to give either false positive or false negative results, or to output an incorrect detected concentration value. Accurately measuring a specific sample area can involve demarcating a test area of the surface to be tested and then sampling the entire demarked area. Existing sampling systems require the test operator to measure out test area dimensions and place physical markers, such as adhesive dots, to define a rectangular test area. The test operator of such existing systems is then responsible for ensuring that the entire area is swabbed before cleaning up the markers. This approach has a number of drawbacks including requiring a lengthy setup, being subject to measurement and marker placement errors, and increasing the risk of exposure of the test operator to potential hazardous drug contamination through placement and removal of the markers.

These and other problems are addressed in embodiments of the hazardous drug collection and detection systems described herein, which involve precise sampling techniques for increasing pickup or shedding efficiency during sampling of a test area on a test surface. A user can use an absorbent swab to absorb buffer solution from a test area demarcated by a template. The sampling techniques can include speed and force protocols indicating swab speed limits (e.g., minimum and/or maximum speed for swab movements during a sampling procedure) and force requirements (e.g., minimum and/or maximum force the user should apply to the swab during the sampling procedure) to improve pickup efficiency. The sampling techniques can include inversion protocols for inverting a container enclosing the swab after the swab absorbs the buffer solution to improve shedding efficiency. The present technology thus improves the accuracy of procedures that identify the presence of and measure the concentration of antineoplastic drugs, including trace amounts of antineoplastic drugs, compared to existing systems. The disclosed swabbing protocols enable more accurate sampling from the tested area and result in more precise test results, for example by the reducing variability in pickup and shedding efficiency variables. A detection system is capable of accurately detecting quantities of even trace amounts of antineoplastic agents based on the known sampled area and of providing results quickly (including immediately after collection). Advantageously, testing and detection can occur at the location of the collection so that immediate, quantitative assessment of contamination level can be determined without the delay required for laboratory sample processing.

Accordingly, one aspect relates to method of collecting a sample of a hazardous contaminant from a test surface, the method comprising obtaining a collection device comprising a handle coupled to an absorbent swab material; demarcating a test area on the test surface; and wiping the test area with the absorbent swab material according to a specified swabbing protocol, wherein according to the swabbing protocol the wiping includes maintaining at least a two pound force on the absorbent swab material as it contacts the test surface.

In some embodiments of the method, according to the swabbing protocol the wiping includes maintaining at least a five pound force on the absorbent swab material as it contacts the test surface. Some embodiments of the method further comprise applying the at least two pound force on the absorbent swab material via the handle.

In some embodiments of the method, the wiping comprises sliding the absorbent swab material along the test surface in a plurality of strokes, each stroke spanning a first dimension of the test area and the plurality of strokes collectively spanning a second dimension of the test area perpendicular to the first dimension. In some further embodiments, according to the swabbing protocol each stroke is performed for a predetermined duration of time. In some further embodiments, according to the swabbing protocol each stroke is performed at a speed less than or equal to a threshold speed. In some further embodiments, according to the swabbing protocol each of the plurality of strokes is oriented along a common orientation.

In some embodiments, the collection device comprises a sealable vial having an interior well shaped to substantially match a cross-section of the handle, and the method further comprises inserting the handle and absorbent swab material into the interior well; sealing the vial; and agitating the absorbent swab material by inverting the vial according to a specified inversion protocol. In some further embodiments, according to the inversion protocol the agitating comprises performing a specified number of cycles, each cycle comprises holding the vial in a first configuration; inverting the vial approximately 180 degrees into a second configuration; pausing movement of the vial for a specified amount of time; and returning the vial to the first configuration. Some further embodiments further comprise removing a cap of the sealable vial; dispensing at least a portion of the sample onto an assay; and determining a test result based on the assay, the test result representing a presence or concentration amount of the hazardous contaminant on the test surface.

Another aspect relates to a method of collecting a sample of a hazardous contaminant from a test surface, the method comprising obtaining a collection device comprising a handle coupled to an absorbent swab material; demarcating a test area on the test surface; and wiping the test area with the absorbent swab material according to a specified swabbing protocol, wherein according to the swabbing protocol movement of the handle during the wiping does not exceed a speed of 100 millimeters per second.

In some embodiments of the method, the wiping does not exceed a speed of 50 millimeters per second. In some embodiments of the method, according to the swabbing protocol, movement of the handle during the wiping further comprises applying at least a two pound force on the absorbent swab material via the handle.

In some embodiments of the method, the wiping comprises sliding the absorbent swab material along the test surface in a plurality of strokes, each stroke spanning a first dimension of the test area and the plurality of strokes collectively spanning a second dimension of the test area that is perpendicular to the first dimension. In some further embodiments, according to the swabbing protocol each of the plurality of strokes is oriented along a common orientation.

In some embodiments the collection device comprises a sealable vial having an interior well shaped to substantially match a cross-section of the handle, and the method further comprises inserting the handle and absorbent swab material into the interior well; sealing the vial; and agitating the absorbent swab material by inverting the vial according to a specified inversion protocol. In some further embodiments, according to the inversion protocol, the agitating comprises performing a specified number of cycles, and each cycle comprises holding the vial in a first configuration; inverting the vial approximately 180 degrees into a second configuration; pausing movement of the vial for a specified amount of time; and returning the vial to the first configuration. In some further embodiments, the method further comprises removing a cap of the sealable vial; dispensing at least a portion of the sample onto an assay; and determining a test result based on the assay, the test result representing a presence or concentration amount of the hazardous contaminant on the test surface.

Another aspect relates to a method of extracting a sample of a hazardous contaminant from an absorbent swab material, the method comprising inserting a handle coupled to the absorbent swab material into a sealable vial having an interior well shaped to substantially match a cross-section of the handle after wiping a test surface with the absorbent swab material according to a specified swabbing protocol; sealing the vial; and agitating the absorbent swab material by inverting the vial according to a specified inversion protocol.

In some embodiments of the method, according to the inversion protocol the agitating comprises performing a specified number of cycles, and each cycle comprises holding the vial in a first configuration; inverting the vial approximately 180 degrees into a second configuration; pausing movement of the vial for a specified amount of time; and returning the vial to the first configuration. In some further embodiments, according to the inversion protocol the inverting lasts approximately one second, the pausing lasts approximately one half of a second, and the returning lasts approximately one second.

BRIEF DESCRIPTION OF THE DRAWINGS

The disclosed aspects will hereinafter be described in conjunction with the appended drawings and appendix, provided to illustrate and not to limit the disclosed aspects, wherein like designations denote like elements.

DETAILED DESCRIPTION

Figure 1A:
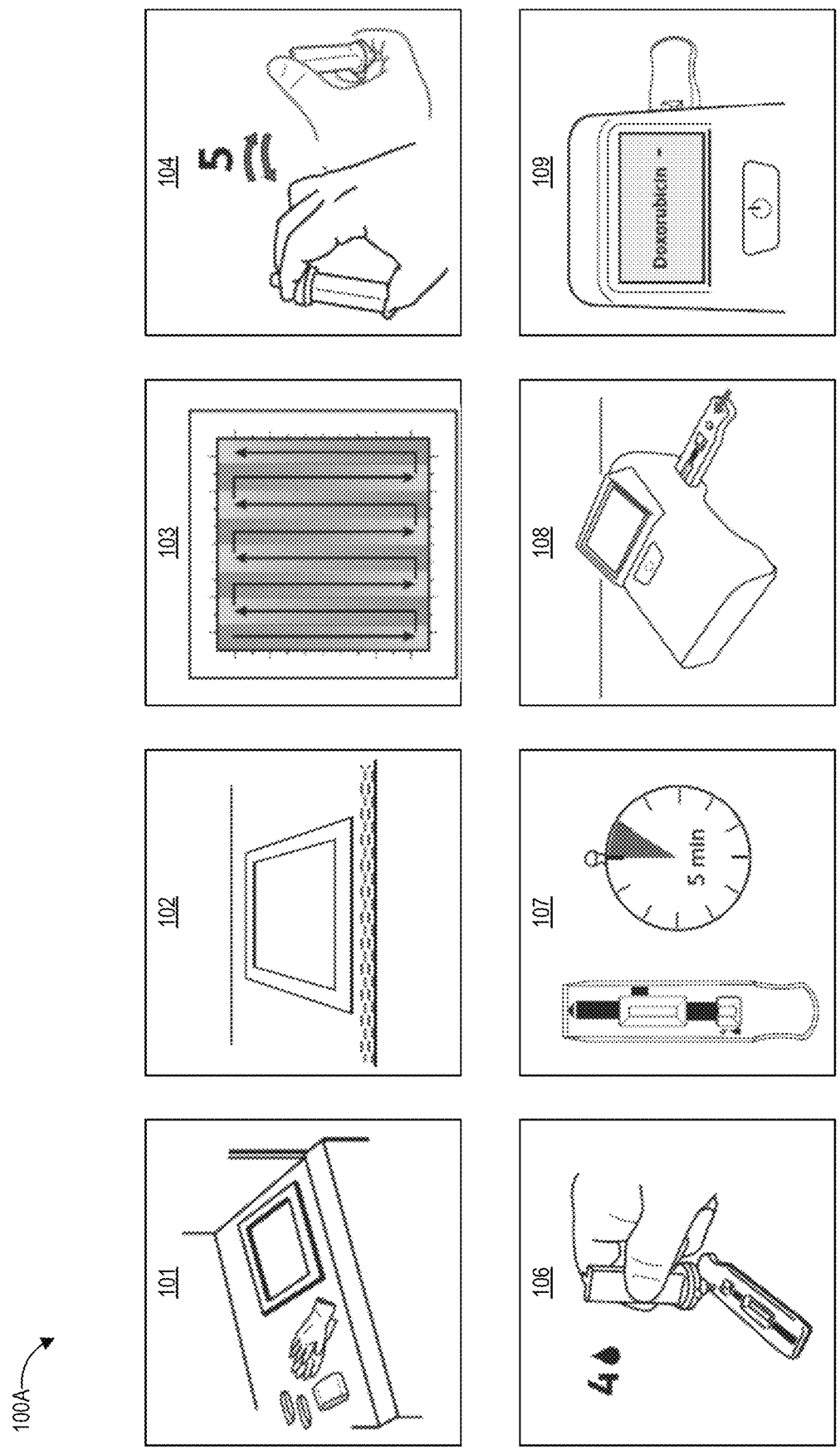
FIGS. 1A-1D graphically illustrate steps of an example method of collecting and testing a liquid sample as described herein.

Embodiments of the disclosure relate to systems and techniques for detection of hazardous environmental contaminants, such as but not limited to antineoplastic drugs used in the treatment of cancer, with increased sensitivity to trace concentrations of antineoplastic drugs in collected samples. A kit for such testing can include a collection system, a testing device, and instructions for use that instruct a user to perform a sampling procedure using specifically-defined swabbing speed, force, and post-swabbing inversion protocols. When implemented as outlined in the instructions for use, these protocols result in the user performing a precise sampling procedure, thereby reducing variation in pickup and shedding efficiency. Throughout this disclosure, example systems, kits, and methods will be described with reference to collection, testing, and detection of antineoplastic agents, but it will be understood that the present technology can be used to collect, test, and detect any particle, molecule, or analyte of interest. Additionally, throughout this disclosure, example systems, kits, and methods will be described with reference to a fluid, such as a buffer solution, that can be applied to a test surface before a collection procedure begins or as a pre-wetted swab is applied to the test surface during the collection procedure. It will be understood, however, that the swabbing and inversion protocols described herein can result in high pickup efficiencies without the use of a fluid, such as a buffer solution, during the collection procedure. Similarly, throughout this disclosure, example systems, kits, and methods will be described with reference to a fluid, such as a buffer solution, enclosed within a collection vial that encloses swab material after the swab material has been swabbed across a test surface and collected analyte of interest, if present, from the test surface. It will be understood, however, that the inversion protocols described herein can result in high shedding efficiencies without the use of a buffer solution, or any fluid, enclosed within a collection vial. The collection vial can contain any suitable medium that allows analytes of interest collected on the swab material to be expressed from the collection vial onto a test device, for example but not limited to a gaseous medium (such as ambient air), a highly viscous liquid medium (such as a gel), and a particulate medium (such as a powder).

A precise method of demarcating and sampling from a specified area can be important in order to obtain an accurate test result in the form of drug mass per square unit area (e.g., nanograms per square centimeter). For example, a sample can be collected from a test surface by using a buffer liquid to wet the surface and using a swab to absorb the buffer liquid and any particles of hazardous drug contamination. Alternatively, any particles of hazardous drug contamination can be collected by wiping the surface with a swab pre-wetted with the buffer solution. When the sample is tested, a test device may be able to identify the concentration of the hazardous drug in the volume of the liquid sample. In order to convert this measurement into a measurement of drug concentration on the test surface, some implementations can use the following formula:

$$\alpha = (C v_b)/(A \eta_p \eta_e)$$

where $\alpha$ represents the contamination surface density (e.g., $ng/cm^2$), C represents the concentration of the sample in the liquid sample, $v_b$ represents the fluid volume of the buffer solution used to collect the sample, A represents the surface area swabbed, $\eta_p$ represents the pick-up efficiency of the swab material and buffer solution, and $\eta_e$ represents the extraction efficiency of contaminant picked up by the swab material. The goal is to have a high concentration signal with low variability, however noise (e.g., variation) in these variables can cause the test to generate either false positive or false negative results. The disclosed techniques provide guidance for reducing the variation in the efficiency terms of the above concentration formula, leading to heightened accuracy in sample testing, and in particular to a more accurate contamination surface density measurement.

Embodiments of the systems and methods described herein can advantageously determine two important aspects regarding contamination of a tested surface quickly and with high precision. First, the disclosed systems and methods can determine the presence of even a very small amount of a hazardous contaminant. This provides an important benefit over other sampling techniques that do not control efficiency variabilities, because if there are just a few molecules on the surface, the sampling swab may miss the molecules entirely if the user does not sample the test area in a regular, constrained, precise way. Sampling with high efficiency variability can lead to a false negative, leading to a missed opportunity to fix a leak or breach of protocol. In one example, the false negative reading may lead to healthcare workers continuing work in the tested area, resulting in their exposure to the hazardous contaminant. The disclosed technique can aid users in reliably sampling potentially contaminated areas. Embodiments of the sampling protocols described herein can ensure the user is reliably informed of the presence of even small amounts of hazardous agent, for example by guiding the user to perform a thorough sampling such that the results provided by test devices are more accurate than results based on other sampling methods.

Second, the disclosed systems and methods can be used to more precisely determine the concentration of a detected hazardous contaminant by reducing variability in the pickup efficiency and shedding efficiency parameters of the concentration formula described above. This is important because the presence of a very small or trace concentrations of certain hazardous drugs may be tolerable or even expected within an environment in some scenarios, but the difference between a smaller, acceptable trace concentration and a larger, unacceptable and potentially dangerous trace concentration may be very small (e.g., on the order of nanograms per centimeter squared). The disclosed techniques, together with test systems and methods described herein, enable the user to now know very quickly and reliably if the concentration of a hazardous contaminant has elevated to dangerous conditions.

Drugs successfully treat many types of illnesses and injuries, but virtually all drugs have side effects associated with their use. Not all adverse side effects classify as hazardous, however. In the present disclosure, the term "hazardous drugs" is used according to the meaning adopted by the American Society of Health-System Pharmacists (ASHP), which refers to a drug as hazardous if studies in animals or humans have indicated that exposures to them have any one of four characteristics: genotoxicity; carcinogenicity; teratogenicity or fertility impairment; and serious organ damage or other toxic manifestation at low doses in experimental animals or treated patients.

Although described in the example context of ascertaining the presence and/or concentration of hazardous drugs such as antineoplastic agents, it will be appreciated that the disclosed devices and techniques for sampling a test area and guiding user sampling procedures can be used to detect the presence and/or concentration of any analyte of interest. An analyte can include, for example, drugs (both hazardous and non-hazardous), antibodies, proteins, haptens, nucleic acids and amplicons. Although the templates, test systems, and methods described herein are typically described herein with reference to test strips and lateral flow assay reader devices, it will be appreciated that the described templates can be implemented in any detection system that seeks to detect the presence of and/or quantify any particle, molecule, or analyte of interest. The test devices described herein are not limited to lateral flow assay test strips, nor to test strips generally. Any suitable test device can be used with implementations of the templates described herein. Features described herein can be implemented in reader devices that analyze other types of assays, such as but not limited to molecular assays, and provide a test result. Further, the collected fluid can be transferred to a centrifuge, spectrometer, chemical assay, or other suitable test device to determine the presence and/or concentration of the target particle, molecule, or analyte of interest, including but not limited to hazardous substances.

Various embodiments will be described below in conjunction with the drawings for purposes of illustration. It should be appreciated that many other implementations of the disclosed concepts are possible, and various advantages can be achieved with the disclosed implementations.

Overview of Example Sampling Method

FIGS. 1A-1D graphically illustrate steps of an example method of collecting and testing a liquid sample that can be performed using sampling protocols as described herein. FIG. 1A illustrates example steps of a testing method 100A for testing for the presence of an analyte on a test surface. One, some, or all of the depicted blocks of FIG. 1A can be printed as graphical user interface instructions on a template, the packaging of an assay and/or collection kit, or can be presented on a display screen of an assay reader device, a test area terminal, or a personal computing device of the user.

At block 101, the user can identify a sample location and gather a collection kit, assay cartridges, and a template. The collection kit can include a swab attached to a handle and a collection container. In some examples, the swab is pre-wetted with buffer solution and packaged together with the handle in a first sealed pouch and the collection container is packaged in a second sealed pouch. The assay cartridge may include an assay device housed inside a cartridge having a window or port aligned with a sample receiving zone of the assay device. In one implementation, the assay device is a test strip, for example but not limited to a lateral flow assay test strip. Also at block 101 the user can put on clean gloves prior to each sample collection and/or opening of the collection kit, both to protect the user from potential contamination on the surface and to protect the collected sample from contamination with anything on the user's hands.

At block 102, the user can establish a test area on the test surface. For example, the user can place a template over the intended location to clearly demarcate the area that will be swabbed. In some embodiments, block 102 can involve a user removing a central portion of a template to create an open area within a border, peeling the border away from an adhesive backing, and placing the adhesive border on the test surface. Methods described herein can ensure that the edges demarcating the open area are positioned straight and flat on the test surface, which can increase the accuracy of the test result. In some embodiments, block 102 can involve the user activating or being presented with an augmented reality overlay (e.g., via an augmented reality wearable or a laser projected overlay) that places an image of a template over the real-world test area. Also at block 102 the user can open the collection kit packaging, including opening the separately-packaged swab and handle.

The user can swab the test area using slow and firm strokes. As shown, the user can methodically pass the swab in straight strokes along the height of the test area all the way across the width of the test area. As described herein, the direction, speed, and force of the swabbing strokes can follow specified protocols. A template border can include markings that assist the user in maintaining even separation between adjacent swab strokes across the test surface. Such markings may be spaced apart by a distance determined based on a known width of a swab handle provided with the template, such that maintaining alignment of the swab handle with the markings causes the entire test area to be sampled. In some embodiments, the swab handle can additionally have markings, for example at the center point along its width, to further assist the sampling user with maintaining alignment between the swab handle and the template markings.

The test area may be one square foot in some embodiments, for example demarcated as a 12 inches by 12 inches (144 square inches) region. Other examples can use greater or smaller areas for collection including 10 inches by 10 inches, 8 inches by 8 inches, 6 inches by 6 inches and 4 inches by 4 inches, non-square rectangular regions (e.g., a 9 inches by 16 inches rectangle), and non-rectangular regions (e.g. circles). Different sized templates may be specified for usage with different test surfaces, either physical or augmented reality.

At block 104, the user can insert the swab into the collection container. In some examples, the collection container includes a t-shaped well. Though not illustrated, the swab may have a t-shaped cross-section that substantially matches that of the container well. The user seals the container with a top that includes a dripper cap, and fully inverts (e.g., turn upside down and then return to right-side-up) the sealed container five times. During these inversions, the liquid in the well of the container washes primarily over the swab material due to the cross-sectional shape of the well, and the handle slides within the well due to the well having a greater height than the handle. The inversion combined with the geometries of the container and handle and the flow of the buffer solution can extract collected contaminants from the swab material. Block 104 can additionally include following inversion protocols as described herein.

At block 106, the user can leave the swab and handle inside the container, remove the dripper cap, and squeeze (or allow gravity to draw) four drops (or another suitable number of) into the sample well on each assay cartridge. For example, in some embodiments the user may drop sample onto multiple assays each designed to test for a different drug. In some examples anywhere between three and ten drops can produce suitable results on the assay. A drop is an approximated unit of measure of volume corresponding to the amount of liquid dispensed as one drop from a dropper or drip chamber via gravitational pull (sometimes aided by a positive pressure created within the container holding the liquid). Though the precise volume of any given drop depends upon factors such as the surface tension of the liquid of the drop, the strength of the gravitational field pulling on the drop, and the device and technique used to produce the drop, it is commonly considered to be a volume of 0.05 mL. In alternate embodiments the user may mechanically couple a fluid transfer portion of the collection device to a fluid transfer portion of the assay device to release a controlled volume of sample through a closed fluid pathway.

At block 107, the user can use a timer to allow the sample to develop for a period of time. For example, the sample can develop for about one minute, about two minutes, about three minutes, about four minutes, about five minutes, about six minutes, or some other amount of time. Other development times are possible. In some embodiments the timer can be built in to the programming of the reader device that reads the assay. The development time can vary depending on the particular test that is being performed and the particular operating parameters of the assay device.

At block 108, the user can insert the assay cartridge into an assay reader device. The assay cartridge can be inserted into the ready device prior to or after the sample is developed, depending upon the operational mode of the device. In some embodiments, the user may sequentially insert multiple cartridges for testing different aspects of the sample or for ensuring repeatability of test results.

At block 109, the assay reader device reads portions of the inserted cartridge (including, for example, detecting optical signals from exposed areas of a capture zone of a test strip housed in the cartridge), analyzes the signals to determine optical changes to test zone location(s) and optionally control zone location(s), determines a result based on the optical changes, and displays the result to the user. The device can optionally store the result or transmit the result over a network to a centralized data repository. As illustrated, the device displays a negative result for the presence of Doxorubicin in the sample. In other embodiments the device can display a specific detected concentration level in the sample and/or determined for the test area, and optionally can display confidence values in the determined result.

Embodiments of the reader devices described herein can determine the presence or the absence of a hazardous drug on a tested surface with a high degree of confidence, and display an indication of this test result to a user very quickly (in some instances, within 1 to 2 minutes) after the user tests the surface. In some cases, the reader device can determine a concentration of contamination and display an indication of the determined concentration to the user very quickly (in some instances, within 1 to 2 minutes) after the user tests the surface. In still further examples, the reader device correlates a detected level of contamination with a risk of human uptake and/or risk of harmful exposure to humans. To illustrate in one non-limiting example, an unintended human uptake of 1.0 $ng/cm^2$ of Cyclophosphamide, a hazardous antineoplastic drug, can be deemed a harmful exposure and/or exposure to a carcinogen. It will be understood that a different level of contamination of Cyclophosphamide could be established as a threshold for harmful exposure, and that the level of contamination for various antineoplastic drugs can be set to different levels depending on the needs of the user and the testing environment.

In this example, the reader device is configured to detect a level of contamination of Cyclophosphamide for a 12 inch by 12 inch (just as an example) sampled area that is $1/10^{th}$ of this 1.0 $ng/cm^2$ threshold level of Cyclophosphamide contamination, or 0.1 $ng/cm^2$. For example, the dynamic range of the assay test device (and reader devices described herein that read the disclosed assay devices) can be capable of detecting a level of contamination of Cyclophosphamide as low as about 0.1 $ng/cm^2$ per 12 inch by 12 inch sample test area. In one non-limiting embodiment, the reader device is configured to display an indication of an actual measured concentration of Cyclophosphamide. For example, a display on the reader device may display the reading "0.085 $ng/cm^2$" to the user upon completion of reading the test device. In another non-limiting embodiment, the reader device is configured to indicate a binary result to the user based on an actual measured concentration of Cyclophosphamide. For example, a display on the reader device may display the reading "−" or "−Cyclophosphamide" to the user upon completion of reading the test device when the actual measured concentration of Cyclophosphamide is less than about 0.1 $ng/cm^2$ (equivalent to a 93 ng mass of Cyclophosphamide for a 12 inch by 12 inch test sample area). The display on the reader device may display the reading "+" or "+Cyclophosphamide" to the user upon completion of reading the test device when the actual measured concentration of Cyclophosphamide is about 0.1 $ng/cm^2$ or greater (equivalent to a 93 ng mass of Cyclophosphamide for a 12 inch by 12 inch test sample area).

In some examples, the reader device is configured to correlate an actual measurement of contamination with a risk of human uptake and/or risk of harmful exposure to humans and to display an indication of the risk to the user upon completion of reading the test device. For instance, the reader device may be configured to correlate an actual measured concentration of Cyclophosphamide of less than about 0.1 ng/cm$^2$ as a reading within a window of acceptable error and/or with a low risk of harmful exposure. In this case, the reader device can display a reading of "No further action" to the user. The reader device can be configured to correlate an actual measured concentration of Cyclophosphamide of about 0.1 ng/cm$^2$ (equivalent to a 93 ng mass of Cyclophosphamide for a 12 inch by 12 inch test sample area) with a moderate risk of harmful exposure. In this case, the reader device can display a reading of "Notify others; Begin Decontamination" to the user. The reader device can be configured to correlate an actual measured concentration of Cyclophosphamide of greater than 0.1 ng/cm$^2$ (equivalent to a 93 ng mass of Cyclophosphamide for a 12 inch by 12 inch test sample area) as a reading within a window of unacceptably high contamination. In this case, the reader device can display a reading of "Evacuate immediately" to the user. The reader device may also automatically transmit a warning or alert to the user with a warning sound or light (for example, a voice prompt or bright flashing light); transmit a warning or alert to other personnel within a distance of the reader device and the tested surface (for example, initiate voice prompts to evacuate the immediate area, emit a high-decibel siren, etc.); and/or transmit a warning or alert to personnel within or outside the physical location where the test event occurred (transmit, via a wired or wireless connection, an emergency notification to a head pharmacist, nurse, manager, safety officer, or regulatory agency that includes location of the test event, hazardous drug name, and the measured concentration of the hazardous drug). These examples are not intended to be limiting and it will be understood that other concentrations, thresholds, display readings, and warnings can be implemented in the systems described herein.

After testing the user can re-seal the container with a dripper cap and dispose of the collection device and assay (for example in compliance with hazardous waste regulations). Optionally, the user can execute any needed decontamination procedures, re-test a decontaminated surface, and perform required reporting of the result.

Figure 1B:
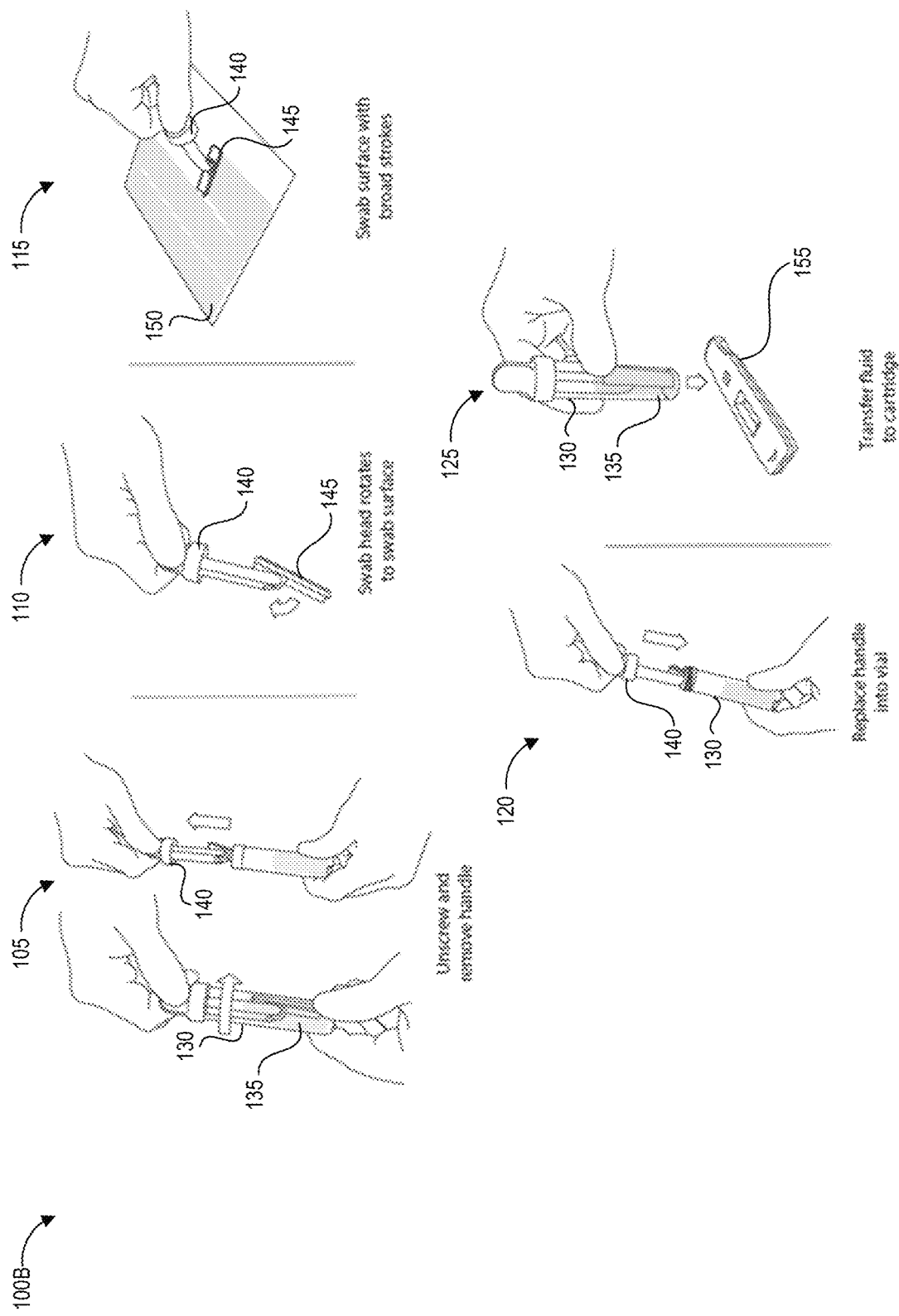

FIG. 1B illustrates another testing method 100B that depicts details of steps 103, 104, and 106 of the process 100A using an alternate embodiment of the collection device.

The method 100B begins at step 105, in which a user can remove a handle 140 from a container 130 containing a predetermined volume of buffer fluid 135. The handle 140 has a swab 245 secured to one end that is pre-wetted with the buffer fluid 135. In other implementations, the user can separately apply a fluid that did not originate from the container 130 to the test surface. For example, the buffer fluid 135 can be provided separately, applied to the test surface, and absorbed using the swab 145. The buffer fluid 135 helps lift contaminants from the test surface into the swab.

At step 110, optionally in some embodiments the swab head can rotate to assist in making and maintaining contact between the swab 145 and the test surface 150.

At step 115, the user can swab a designated test area of the test surface 150 following specified swabbing protocols according to the present disclosure. It will be understood that the specific parameters of swabbing protocols described herein are example parameters that yield very accurate test results, that the specific parameters are not intended to be limiting, and additional swabbing protocol parameters may be implemented to yield very accurate test results. It can be preferable in some implementations to swab the test area slowly and firmly enough to yield a reliable and high pickup efficiency, particularly for contaminants where even small quantities per area are harmful to users. The disclosed speed and force protocols can be used to guide a user to sample the test area in a manner that yields this reliable and high pickup efficiency. Reducing variability in pickup efficiency can also allow a reader device as described herein to generate an accurate measurement of the concentration of the contaminant per unit area in situations where a very small amount of contaminant is present. Even if the amount of contaminant detected is very small and not immediately harmful to persons in the immediate area, detection of contaminant in any amount can alert the user to a leak or unintended release of hazardous material. Further, for some hazardous drugs there is no safe exposure level. As such, some embodiments of step 115 can involve adhering to specified swabbing protocols as described herein.

At step 120, the user can insert the swab 145 and handle 140 into the collection container 135 and seals the collection container 135 to create a sealed container. Also, at step 120, the user can invert the sealed container following specified inversion protocols according to the present disclosure. Optionally, the user and/or structure of the container can agitate the swab to release collected contaminants into the fluid within the container 135. It will be understood that the specific parameters of inversion protocols described herein are example parameters that yield very accurate test results, that the specific parameters are not intended to be limiting, and additional inversion protocol parameters may be implemented to yield very accurate test results. Some embodiments of step 120 can involve adhering to specified inversion protocols as described herein to increase shedding efficiency and decrease variability in shedding efficiency.

At step 125, the user can transfer fluid to a test device, such as but not limited to a cartridge 155 containing a lateral flow assay including a test strip. For example, the user can drip fluid from the container 130 onto a sample receiving zone of the test strip. In some embodiments, the cartridge 155 (or other test system) and container 130 can be structured to mechanically mate via a fluid-tight connection so as to prevent accidental exposure of potentially contaminated fluid to users and/or the testing environment.

Figure 1C:
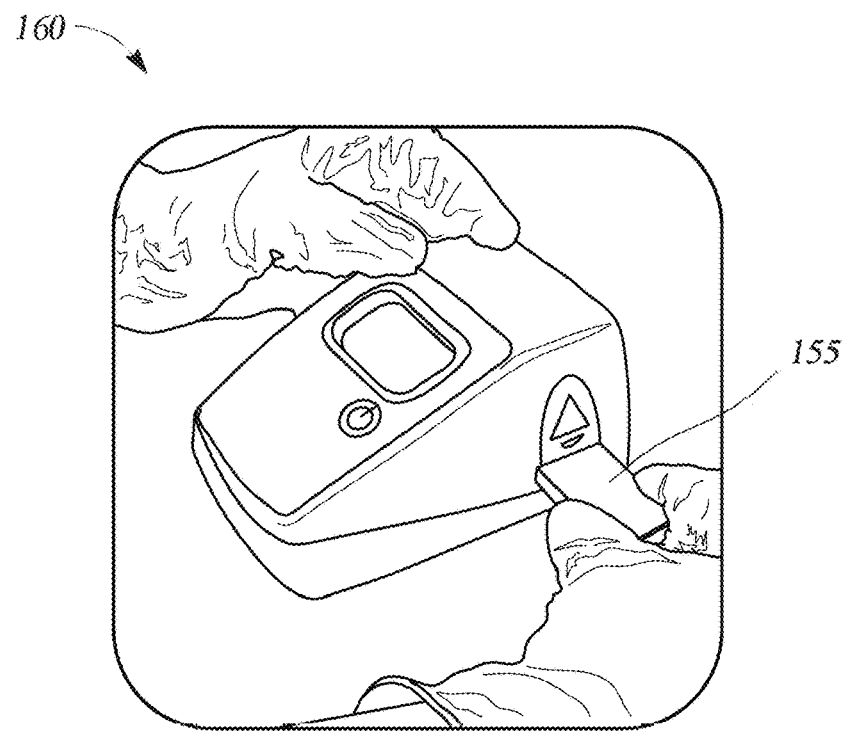
Figure 1D:
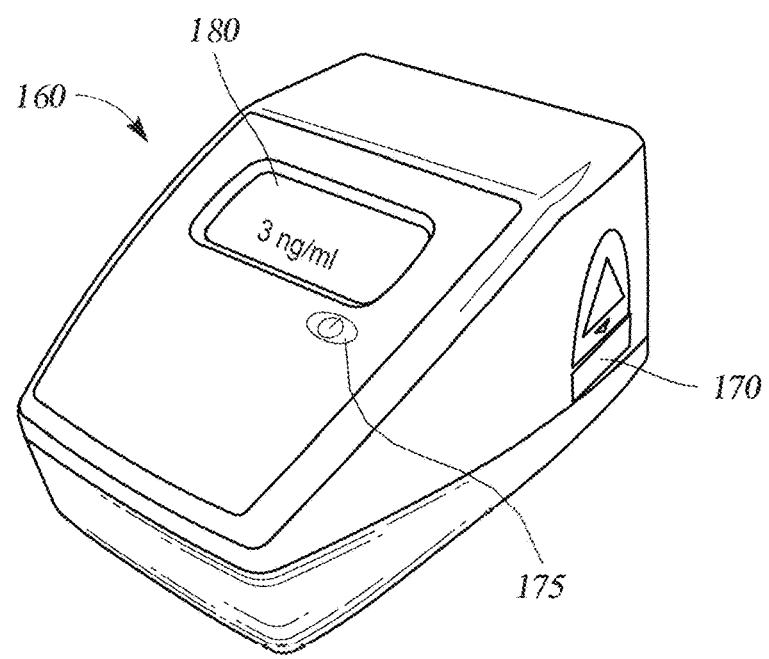

FIG. 1C illustrates a further step of inserting the cartridge 155 into an aperture 170 of reader device 160. Although the following example is described with reference to reader device 160, an assay test device (whether housed within cartridge 155 or not housed within a cartridge) can be read by any suitable reader as described above. Further, though not illustrated, further steps can include operating the reader device 160 to detect a result of the test (for example, by imaging the test strip or detecting an optical change that occurred on the test strip), analyze the test result, and display results of the test. FIG. 1D illustrates the reader device 160 displaying a test result on display 180. In this case, the test result indicates a concentration of the analyte of interest of 3 ng/ml.

The device 160 can be an assay reader device having an aperture 170 for receiving an assay test strip and cartridge 155 and positioning the test strip so that the detection zones are positioned in the optical path of detection components located inside the device 160. In some cases, the detection components can include imaging components that image portions of the assay test strip and cartridge 155 to detect optical changes in the assay test strip. The device can also use these or additional imaging components to scan a bar code on the cartridge, for example to identify which detection techniques and analysis to perform.

Some embodiments of the device 160 can be configured to perform an initial scan using a barcode scanner to scan one or more bar codes, for example provided on templates, on cartridges inserted into the aperture 170 or on separate identifiers. A barcode can identify the type of test to be performed, the template used for sampling, the person conducting the test, the location of the test, and/or the location in the facility of the test surface (for example pharmacy, nursing area, cabinet #, bed #, chair #, pump #, etc.). After reading any barcode identifiers the cartridge 155 is then inserted into the reader as shown in FIG. 1C. Barcodes are provided as an illustrative example, and in various embodiments other identification patterns can be provided for reading by the device 160, for example serial numbers, graphical identifiers, radio frequency ID transmitters, and the like.

The device 160 can include a button 175 that readies the device for use and provides an input mechanism for a user to operate the device. In some embodiments device operation mode can be set via a number or pattern of clicks of the single button 175 of the device 160. For example, in some implementations a single press of the button 175 can power on the device 160 and set the device 160 to a default operation mode, and the device 160 can implement the default operation mode upon insertion of a cartridge. A double click of the button 175 can initiate an alternate operation mode that is different than the default operation mode. Other numbers or patterns of pressing the single button 175 by a user can provide instructions to the processor of the device regarding a desired operation mode. Embodiments of a device 160 are described herein with reference to a single button, but other features allowing a user to select and switch between device operation modes are possible (such as but not limited to a single switch, knob, lever, or handle).

One example of a device operation mode is end-point read mode. In the end-point read mode, the user prepares and incubates the assay outside of the device 160 and tracks the development time of the assay. For example, an assay for determining Methotrexate or Doxorubicin concentration can have a development time of 5 minutes, so the user would apply the fluid to the assay from a collection device as described herein and wait for 5 minutes. At the end of the 5 minutes the user would insert the assay 155 into the device 160 to obtain a test result. Accordingly, when operating in end-point read mode the device 160 can provide instructions, for example audibly or on a visual display, that instruct a user to wait for a predetermined time after applying a sample to an assay before inserting the assay in the device 160. In other embodiments, when operating in end-point read mode, the device 160 may not display any instructions but may simply read an assay upon insertion into the device 160. Upon insertion of the assay into the base device 160, an optical reader of the device can collect data (for example, image data) representing the assay for analysis in determining a result of the assay. In some embodiments end-point read mode can be the default operation mode of the device 160.

Another example of a device operation mode is walkaway mode. When operating in walkaway mode, the device 160 can provide instructions for the user to insert the assay immediately after application of the sample. In the walkaway mode according to one embodiment, the user can apply the specimen to the assay and immediately insert the assay into the device 160. The assay will develop inside the device 160 and the device 160 can keep track of the time elapsed since insertion of the assay 155. At the end of the predetermined development time, the device 160 can collect data representing optical changes in the assay, analyze the data to determine a test result, and report the test result to the user. The assay development time can be unique to each test. In some embodiments walkaway mode can be set by double-clicking the single button 175 of the device 160. Further input can indicate the assay development time to the reader device. For example, a barcode scanned by a barcode reader, or a barcode provided on the assay or on a cartridge used to hold the assay, can indicate to the device 160 a type of assay that is inserted and a development time for that assay. Based upon the type of assay, the device 160 can wait for the predetermined amount of time after sample application and insertion before collecting data representing optical changes in the assay.

There are many advantages associated with the ability of a user to select and switch between device operation modes in implementations of assay analyzers described herein. The endpoint read mode can be convenient in large laboratories or medical practice facilities where personnel typically batch process a number of tests. The walkaway mode can be useful when a single test is being performed, or when the end user does not want to have to track the assay development time (or is not knowledgeable or not trained on how to track the assay development time accurately). The walkaway mode can advantageously reduce or eliminate the occurrence of incorrect test results due to an assay being inserted and read (for example, imaged) too quickly (too soon before the development time of the assay has elapsed) or too slowly (too long after the development time of the assay has elapsed). Further, in walkaway mode the assay reader can operate to inspect the assay (for example, capture multiple images of the assay) at predetermined time intervals, for example when a kinetic graph of the assay readings is desired.

One embodiment of the disclosed device 160 includes only a single button 175 on its exterior housing, such as a single power button that powers the device 160 off and on. Embodiments of the disclosed device 160 also implement two different device operation modes (although more than two device operation modes are possible). In order to enable the end user to select and switch between the two device operation modes, the device 160 can include instructions to implement a double-click function on the power button. After receiving input of a single press of the button to power on the device, insertion of an assay cartridge can automatically trigger end-point read mode. When the processor of the device receives input from a user double clicking the power button, this can initiate the stored instructions to implement the walkaway mode. This double click functionality offers a simple and intuitive way for the end user to switch between different operation modes of the base assay analyzer. The double click functionality also enables the user to configure the device in real time to operate in the walkaway mode without requiring any additional configuration steps or additional programming of the device 160 by the user. It will be appreciated that the device 160 can be provided with instructions to recognize other click modes instead of or in addition to the double click to trigger secondary (non-default) device operation modes, for example to recognize a user pressing the button any predetermined number of times, pressing the button in a predetermined pattern, and/or pressing and holding the button for a predetermined length of time.

As described above, the device 160 can also include a display 180 for displaying instructions and/or test results to the user. After insertion of the test strip, the device 160 can read a bar code on the assay test strip to identify the name, permissible concentration ranges of the drug, and/or maximum permissible concentration of the drug. The device 160 can inspect the inserted test strip (in one example, by "imaging" the strip or otherwise emitting light towards the test strip and then detecting the intensity of a signal representing detected light reflected from the test strip), and analyze the signals representing the inspected test strip to calculate results, display the results to the user, and optionally transmit and/or locally store the results. The results can be calculated and displayed as contamination with an indication of positive or negative (for example, +/−; yes/no; etc.), and/or the actual amount of contamination (analyte of interest) per area (for example, Drug Concentration=0.1 ng/cm$^2$) and/or an actual an actual contamination (analyte of interest) per area (for example, Drug Concentration=0.1 ng/cm$^2$), and/or an actual amount of contamination (analyte of interest) per volume of buffer solution (for example, Drug Concentration=3 ng/ml). These indications are non-limiting examples as other indications and measurement units are also suitable.

Some embodiments of the device 160 may simply display the result(s) to the user. Some embodiments of the device 160 may also store the result(s) in an internal memory that can be recalled, for example, by USB connection, network connection (wired or wireless), cell phone connection, near field communication, Bluetooth connection, and the like. The result(s) can also automatically be logged into the facility records and tracking system of the environment (for example, facility) where the test is performed. The device 160 can also be programmed to automatically alert any additional personnel as required, without further input or instruction by the user. For example, if the device 160 reads contamination levels that are above the threshold of human uptake and considered hazardous to for human contact, a head pharmacist, nurse, manager, or safety officer can be automatically notified with the results and concentration of contamination to facilitate a rapid response. The notification can include location information, such as but not limited to a geographic position (latitude/longitude) or description of location (Hospital A, Patient Room B, etc.). That response may include a detailed decontamination routine by trained personnel or using a decontamination kit provided together or separately from the hazardous contamination detection kit.

In some embodiments, device 160 can be a special-purpose assay reader device configured with computer-executable instructions for identifying trace concentrations of contaminants in the samples applied to test strips. In other embodiments other suitable liquid sample test systems can be used to identify the presence and/or concentration of a hazardous drug.

Overview of Example Devices and Techniques for Test Area Sampling

As described above, specifically-defined methodologies for collecting a sample from a test area can be beneficial or required in order to accurately determine the presence or concentration of trace quantities of hazardous drugs in a test sample. Existing sampling systems require the test operator to measure out test area dimensions and place four adhesive dots on the test surface at the corners of a rectangular test area. The user is then instructed to sample the same area with both vertical strokes and horizontal strokes while taking care not to press too hard on the cotton swab, which typically resembles a stick with a ball of cotton at one end. Any collected sample is then extracted and tested at a laboratory testing facility. This approach has a number of drawbacks including variation in pickup efficiency and extraction performed significantly later after testing (e.g., weeks later) at a remote facility.

The disclosed sampling techniques address these problems by providing the user with sampling protocols including desired swab stroke force and swab stroke speed that reduce variability and maximize the efficiency with which the collection swab picks up molecules of contaminant from the test surface. The disclosed protocols can optimize, for example, the likelihood that all trace contaminants, if present, will be collected on the swab. Advantageously, the disclosed collection swabs include a handle and a base that enable the user to apply sufficient force to the swab material, while also minimizing contact between the user and the sample. The disclosed sampling techniques further address these problems by providing inversion protocols that guide a user in achieving a consistent and high extraction efficiency for extracting collected contaminants from the swab material. In some implementations described herein, the disclosed sampling techniques also address these problems by providing a collection vial with an internal well shaped to substantially match the cross-section of the handle. Beneficially, extraction can occur at the time and location of testing using the disclosed systems and techniques.

Figure 2A:
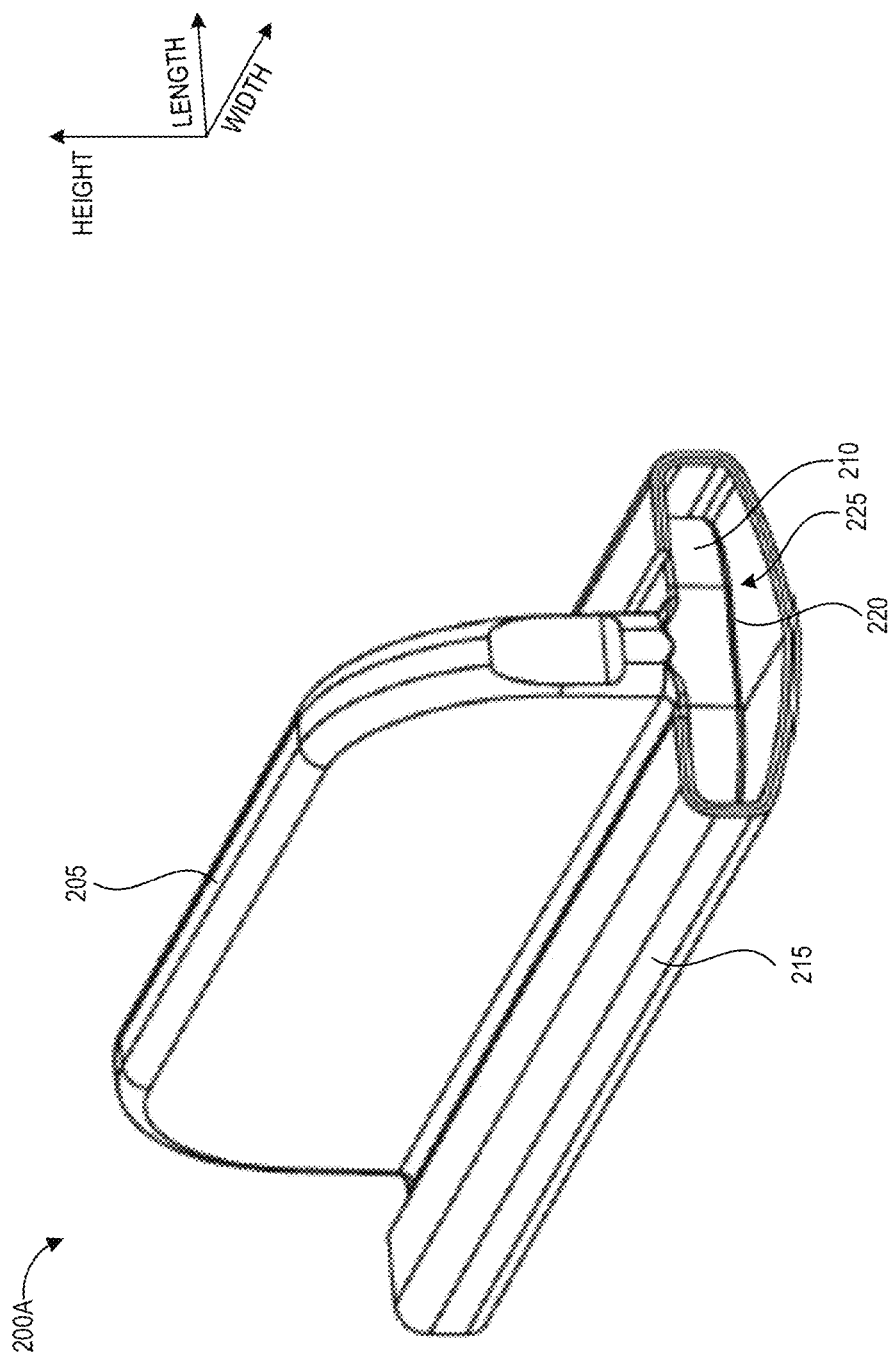
FIG. 2A illustrates an example handle that can be used to sample a test area by embodiments of the disclosed techniques.

FIG. 2A illustrates an example handle 200A secured to swab material 215 that can be used to sample a test area in accordance with techniques described herein. The handle 200A includes a grip portion 205 and a base portion 210 with the swab material 215 wrapped around and secured to the base portion 210, for example via ultrasonic welding, mechanical fasteners, adhesive, or other suitable securing techniques.

As illustrated, the grip portion 205 extends perpendicularly from the center of one face of the base portion 210. The grip portion 205 can extend away from the base portion at other angles and/or from other locations along the width of the base portion 210 in other embodiments. The grip portion 205 can have a height sufficient to keep the fingers of a user away from a surface in contact with the swab material secured to the base portion 210, for example 0.25 inches or more, or 0.5 inches or more, in various embodiments. In one non-limiting example, the height of the grip portion 205 is about 0.525 inches. The grip portion 205 can extend along the full width of the base portion 310 as illustrated, or can extend along just a portion of the width of the base portion 210. In some embodiments the length of the base portion can also assist in shielding the fingers of the user from the test surface, and the length can be for example 0.25 inches or more, or 0.5 inches or more, in various embodiments. In one non-limiting example, the length of the base portion 210 is about 0.55 inches. Embodiments of the base portion 210 with a length of about 0.55 inches can include about 0.2 inches clearance on each side of the grip portion 205 for the user's fingers to grip the handle 200A. This can shield the user's fingers from the test surface below the base portion 210 during use of the handle 200A, and can, for example, act as a stop to prevent the user's fingers from contacting the test surface. Other sizes can be suitable for other embodiments, and the disclosed dimensions are provided to illustrate and not limit the dimensions of the handle 200A.

The swab material 215 is configured to be loose enough to form a gap 225 between the swab material 215 and the adjacent surface of the base portion 210. The gap 225 can enable the swab material 215 to be agitated by buffer solution when shaken within a collection vial in order to extract collected contaminants from the swab material 215 as described herein. The gap 325 can be between 0.25 inches and 0.75 inches in some embodiments. The swab material 215 may be longer than the base 210 of the handle 200A such that around 0.25 inches of swab material 215 extends beyond the edges of the base 310. The base 210 can have a width of around 2 inches in some embodiments.

Figure 2B:
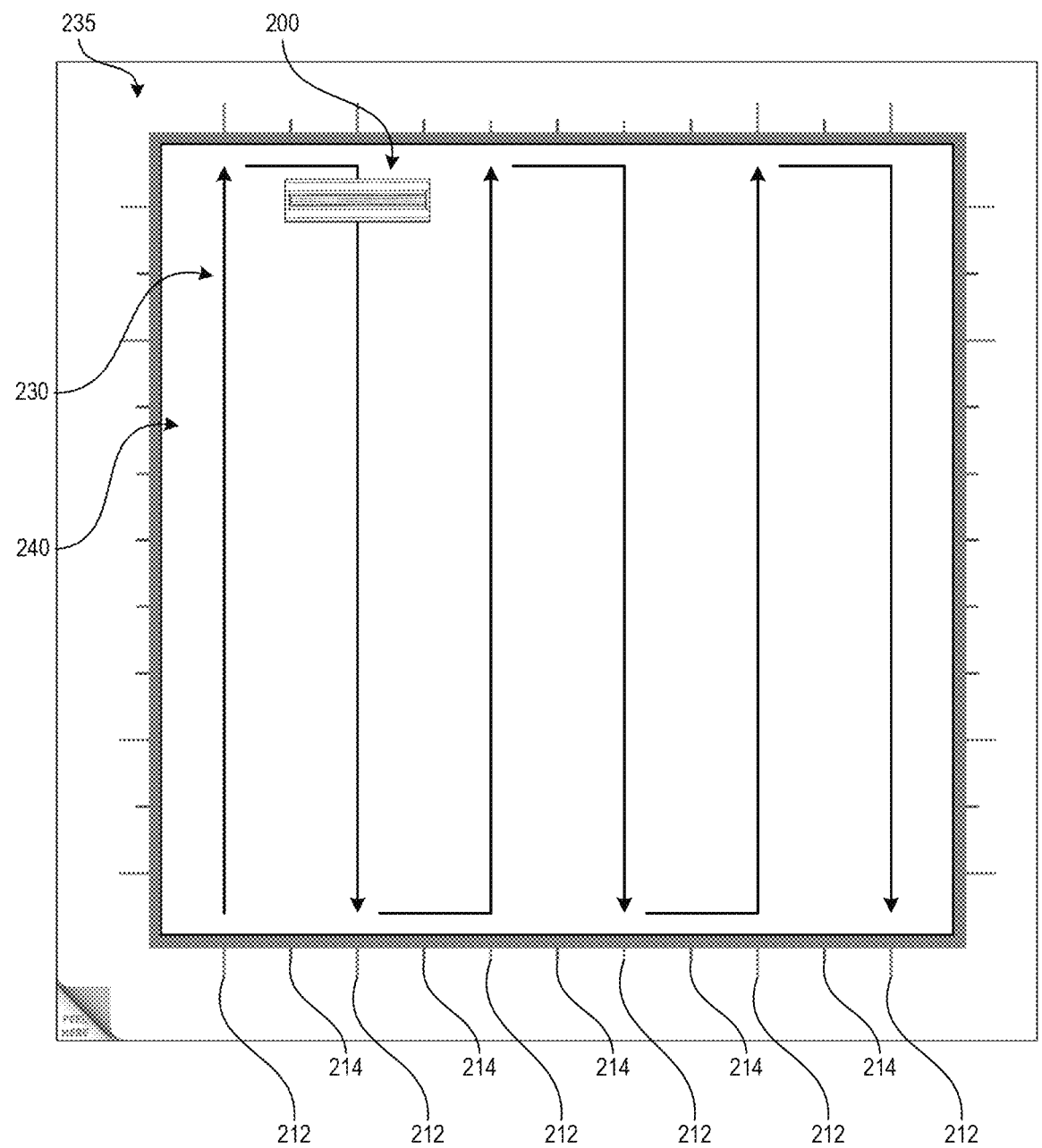
FIG. 2B illustrates an example swabbing pattern using the handle of FIG. 2A with a demarcation template.

FIG. 2B illustrates an example swabbing pattern 230 using the handle 200A of FIG. 2A within the border 210 of an example template. As shown, the user can align the center of the width of the handle 200A with one of a first set of alignment markers 212 provided on the border 210. Two adjacent markers 214 of a second set of alignment markers align with the opposing edges of the width of the base of the handle 200A. In this non-limiting embodiment, the swab material extends a small distance beyond these edges of the base of the handle 200A. In one example, adjacent markers are positioned 1 inch apart, with the first and last markers 212 are each positioned 1 inch from the adjacent interior edge of the border 210. This corresponds to an open area of 12 inches by 12 inches, and in such embodiments the base of the handle 200A can have a width of 2 inches. In such embodiments, with six precise, linear strokes (as shown by the swabbing pattern 230), the user can sample the entire test surface exposed through the border 210 with precision and minimal deviation from the optimal swab pattern.

The user can begin swabbing with the center of the handle 200A aligned with a first alignment marker 212. The user can move the handle 200A in a straight line between the first alignment maker 212 on a first interior edge of the border 210 and a corresponding alignment marker on the opposing interior edge of the border 210. The handle 200A can be in contact with a third interior edge of the border 210 (in the illustrated embodiment, the leftmost interior edge) during this first swab stroke. Once the user has swabbed from the first interior edge of the border 210 to the opposing interior edge, the user can move the center of the handle 200A into alignment with a next alignment marker 212 and can continue moving the swab in a linear fashion along a second line between that alignment marker and the corresponding alignment marker on the first edge. The swab material extending beyond the edges of the base causes a slight overlap between the areas swabbed when the handle 200A is moved along the first line and the second line, and similarly causes overlap between adjacent lines as the handle 200A is moved according to the pattern 230. This overlap beneficially assists the user in swabbing the entire area of the test surface bounded by the border 210. For example, the overlap allows the user to deviate slightly from the intended alignment and still swab the entire test surface. The swabbing pattern 230 described with reference to FIG. 2B is just one example of a suitable swabbing pattern using techniques described herein.

As described herein, each stroke of the swabbing pattern 230 can be performed by moving the swab according to various swabbing protocols. A force protocol can specify a minimum amount of force the user is to exert on the swab during the stroke or can specify a range of acceptable forces. A speed protocol can specify a maximum speed at which the user is to move the swab during the stroke, or can specify a range of acceptable speeds. Stroke speed may be measured based on time taken to move the swab along the stroke from one interior edge of the border 210 to the opposing edge, for example a minimum (or desired) time of 3 seconds for embodiments in which the border 210 demarcates a 12 inch by 12 inch test area.

Figure 2C:
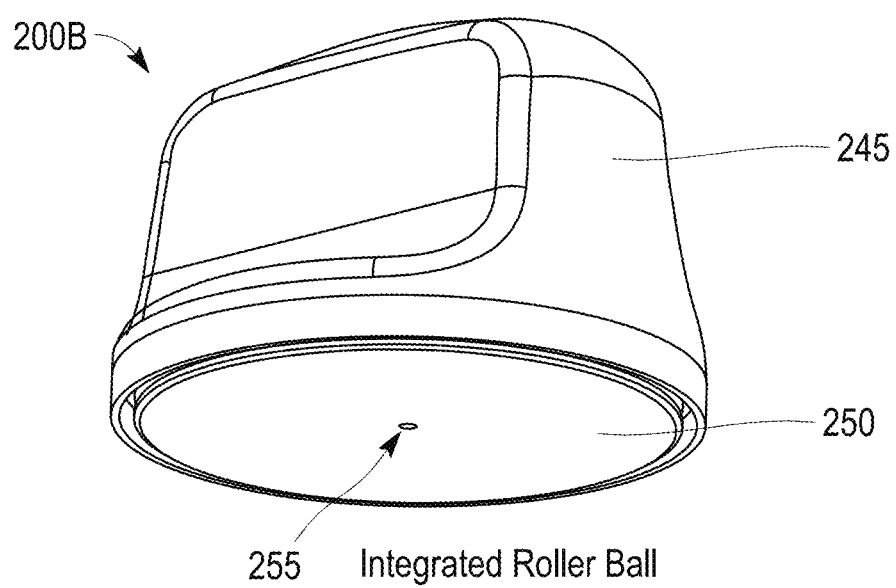
FIG. 2C illustrates another embodiment of the handle of FIG. 2A.

FIG. 2C illustrates another embodiment of the handle 200B that includes a grip portion 245, swab 250, and a roller ball 255 integrated into the swab area to track the speed of swab stroke movement, the force of swab strokes, and/or the distance traveled by the handle 200B. Although not illustrated in FIG. 2C, a handle 200B can include a display for displaying such readings to the user. Some embodiments can include a memory for storing tracked swabbing data (e.g., speed and/or force) and a communications link (e.g., wired or wireless) for communicating tracked swabbing data to a test device. Beneficially, such a handle 200B can be used to provide feedback to users to assist them with maintaining compliance with specified swabbing protocols and to track user compliance with the swabbing protocols.

Example Swabbing Protocol

Figure 3:
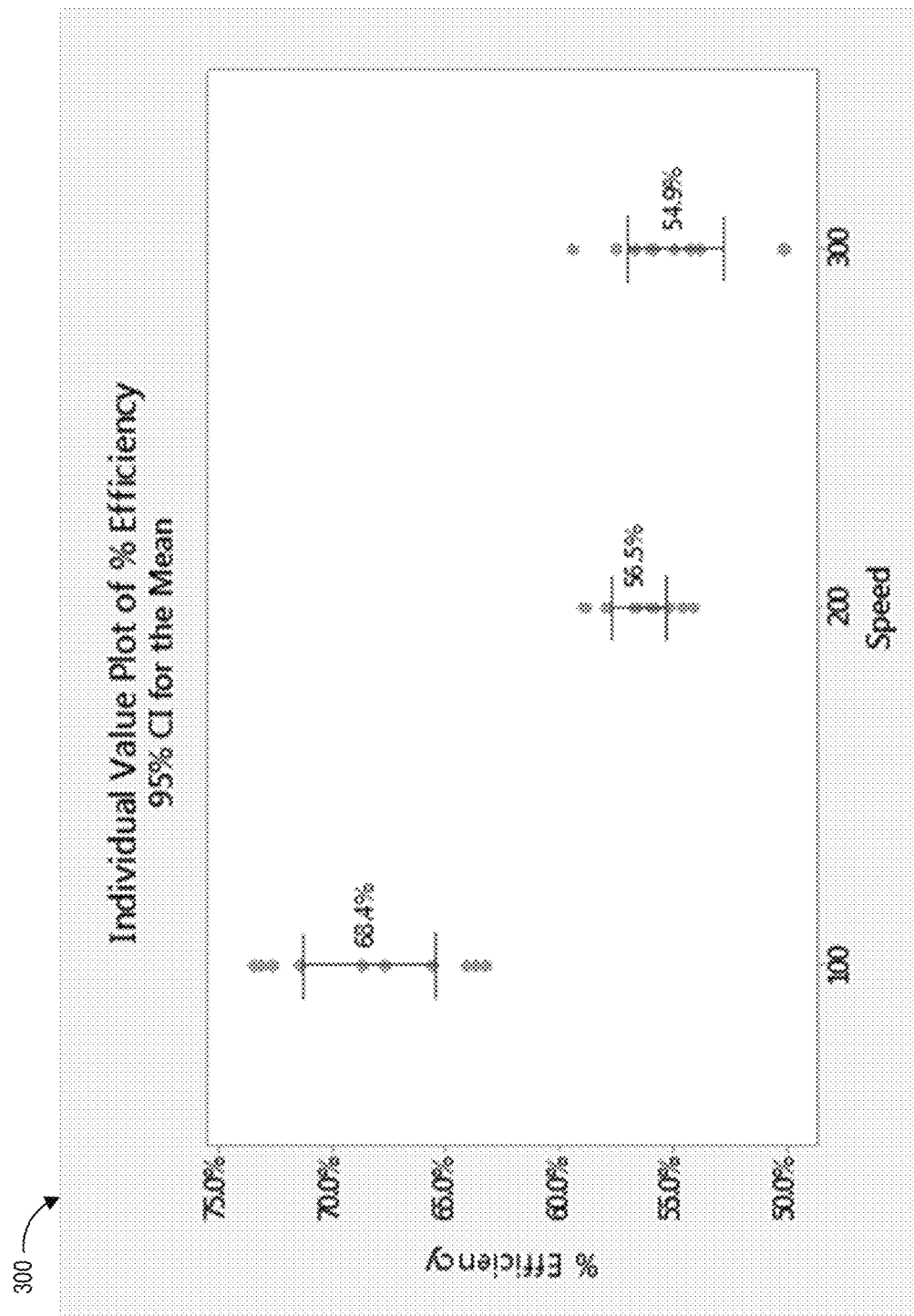
FIG. 3 depicts a plot of data correlating collection swab speed with pickup efficiency according to one example swabbing procedure.

FIG. 3 depicts a plot 300 of data correlating collection swab speed with pickup efficiency according to one example swabbing procedure. Swabbing techniques according to the present disclosure present a number of protocols for a swab user to follow to improve the efficiency terms of the concentration formula above. Increasing the pickup efficiency level can result in lower amounts of variation in pick up efficiency. In some implementations, a low variation may be desired, while in other implementations a higher variation in pick up efficiency may be acceptable if it results in a higher overall efficiency level. Thus, according to the presently disclosed sampling protocols, the pickup efficiency term can be increased to its highest possible level (with low variability) and the concentration term will be more accurate and provide a more precise contamination testing result. If the pickup efficiency is too low, the result can be a false negative result to the end user, leading them to think the surface is free of contaminants when it is not, leading to potential hazardous exposure.

As described above, traditional antineoplastic swab testing uses a cotton swab wetted with a buffer solution to wipe across the surface, relying on the user to press firmly to both wet the surface and pick up any contaminants simultaneously. The swab stroke pattern is usually repeated twice (once in the horizontal direction, and then a second time in the vertical direction). This is an attempt to cover the area twice and pick up as much of the drug on the surface as possible with the cotton tipped swab stick held in the user's hand.

The swabbing handles described herein have been designed with a grip portion and base portion for the swab material, and advantageously does not require the user to hold the swab material directly. Beneficially, this mitigates exposure of the user to potential hazardous contamination. The swabbing handle has also been designed so that the container, used to extract the collected sample from the swab material into a homogenous solution form, fits the handle and the swab to minimize the amount of solution needed, thereby increasing extraction efficiency. These features complement the optimized wiping and extraction processes described herein to maximize accuracy of the test result.

As described with respect to FIG. 1A, the user can first establish the area of the surface to be tested using a template or augmented reality device so that accurate results can be calculated as a contamination rate per unit area. The user then opens a package containing the pre-moistened swab, removes the swab from the package using the grip portion, and begins swabbing the test area. A highly efficient and consistent method of swabbing the test area is to press the swab firmly to the surface and move it in the direction perpendicular to its length along the surface until the end of the test area has been reached. The process is repeated either by lifting up the swab and repeating the process on a second path (in the same direction and next to the first path with a small amount of overlap), or by reversing the direction along the next path (as shown in the example swabbing pattern 230 of FIG. 2B). Through extensive testing and analysis, it was discovered that certain factors of the sampling method have a significant effect on the pickup efficiency (and therefore on the accuracy of the test result). As discussed in detail below, such factors include the speed at which the user moves the collection swab across the surface, and the force with which the user presses down on the collection swab while moving it.

The example plot 300 of FIG. 3 shows pickup efficiency percentage (ranging from 50% to 75%) along its vertical axis and swab speed (measured in millimeters per second) along its horizontal axis. The depicted intervals were calculated based on individual standard deviations. As illustrated, the pickup efficiency improved as the speed decreased from 500 mm/s down to 100 mm/s, and continued to improve as the speed continued to decrease down to 50 mm/s, the slowest tested speed (not illustrated in FIG. 3). A swab movement speed of 50 mm/s is very slow in practice (equivalent to about 6 seconds to move the swab 12 inches) and most users in the test studies did not have the patience to move the swab so slowly. As such, a swab speed protocol according to the present disclosure can set a desired or maximum swab speed to 100 mm/s. This is still a slow movement, but the study that generated the data represented in FIG. 3 indicates that most users will wipe this speed if instructed to. The speed of 100 mm/s takes about 3 seconds per 12 inches of swab stroke. In one embodiment, a template can have an open area bounding a 12 inch by 12 inch region, and thus 12 inches can be the distance of a single swab stroke or wipe. Accordingly, swabbing protocols described herein can instruct the user to count three seconds per stroke or use a timer to track three seconds of time per stroke. This instruction can be easy for the user to count to per row of the swabbing process. The swab speed protocol can vary the instructed time per stroke based on template size in other embodiments.

Figure 4:
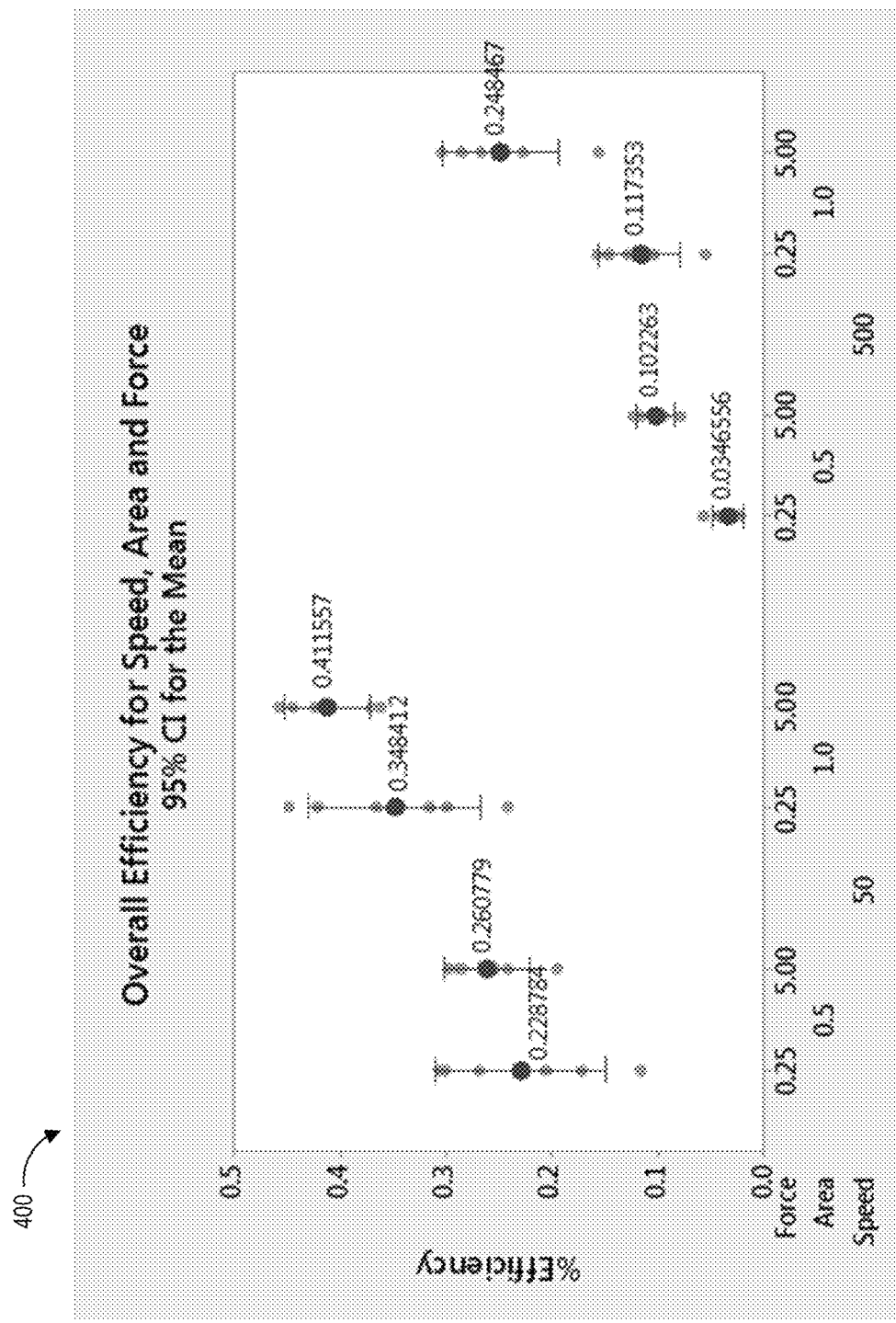
FIG. 4 depicts a plot of data correlating combinations of collection swab speed, force, and swab area with pickup efficiency according to the example swabbing procedure.

FIG. 4 depicts a plot 400 of data correlating combinations of collection swab speed, force, and swab area with pickup efficiency according to the example swabbing procedure. The plot 400 shows pickup efficiency percentage (ranging from 0.0=0% to 0.5=50%) along its vertical axis and various combinations of collection swab speed (measured in millimeters per second), force (measured in pounds), and swab area (representing the area of the swab that is in contact with the test surface, measured in inches squared ($in^2$) along its horizontal axis. The depicted intervals were calculated based on individual standard deviations.

Specifically, the first interval corresponds to a swab force of 0.25 pounds, a swab area of 0.5 $in^2$, and a swab speed of 50 mm/s. The second interval corresponds to a swab force of 5.00 pounds with the same swab area of 0.5 $in^2$ and swab speed of 50 mm/s as the first interval. The third interval corresponds to a swab force of 0.25 pounds, a swab area of 1.0 $in^2$, and a swab speed of 50 mm/s. The fourth interval corresponds to a swab force of 5.00 pounds with the same swab area of 1.0 $in^2$ and swab speed of 50 mm/s as the third interval. The fifth interval corresponds to a swab force of 0.25 pounds, a swab area of 0.5 $in^2$, and a swab speed of 500 mm/s. The sixth interval corresponds to a swab force of 5.00 pounds with the same swab area of 0.5 $in^2$ and swab speed of 500 mm/s as the fifth interval. The seventh interval corresponds to a swab force of 0.25 pounds, a swab area of 1.0 $in^2$, and a swab speed of 500 mm/s. The eighth interval corresponds to a swab force of 5.00 pounds with the same swab area of 1.0 $in^2$ and swab speed of 500 mm/s as the seventh interval.

The first and second intervals, third and fourth intervals, fifth and sixth intervals, and seventh and eighth intervals are depicted together as adjacent pairs of data to illustrate the effect of varying swab force on pickup efficiency. The plot 400 also shows the effects of varying swab stroke speed as discussed above with respect to FIG. 3, as the first through fourth intervals represent higher pickup efficiencies than the corresponding one of the fifth through eighth intervals (here, corresponding intervals have the same force and area combination with different speeds). The plot 400 also shows the effects of swab area, with the third, fourth, seventh, and eighth intervals showing higher pickup efficiencies than the corresponding one of the first, second, fifth, and sixth intervals (here, corresponding intervals have the same force and speed combination with different swab areas).

The amount of force with which the user presses the swab on the surface was found to be another factor having a significant effect on pickup efficiency (and therefore on the accuracy of the test result), as shown in the plot 400 of test sampling procedures. Adjacent pairs of data in the plot 400 show the same area and speed combination first with 0.25 pounds of applied force, and second with 5.00 pounds of applied force. As illustrated by these adjacent pairs of data sets, the 5.00 pound group performed better than the 0.25 pound groups. As such, in some embodiments described herein, force protocols for swabbing can instruct the user to press the swab onto the surface with at least about 5 pounds of force. As with the speed protocol, practical limits on how much force a user can be expected to use come into play. Several user studies revealed that users could be expected to only press constantly with about 2 pounds of force with proper instruction. For this reason, some embodiments of the disclosed fore protocols can indicate that the user should press with at least about 2 pounds of force.

Figure 5:
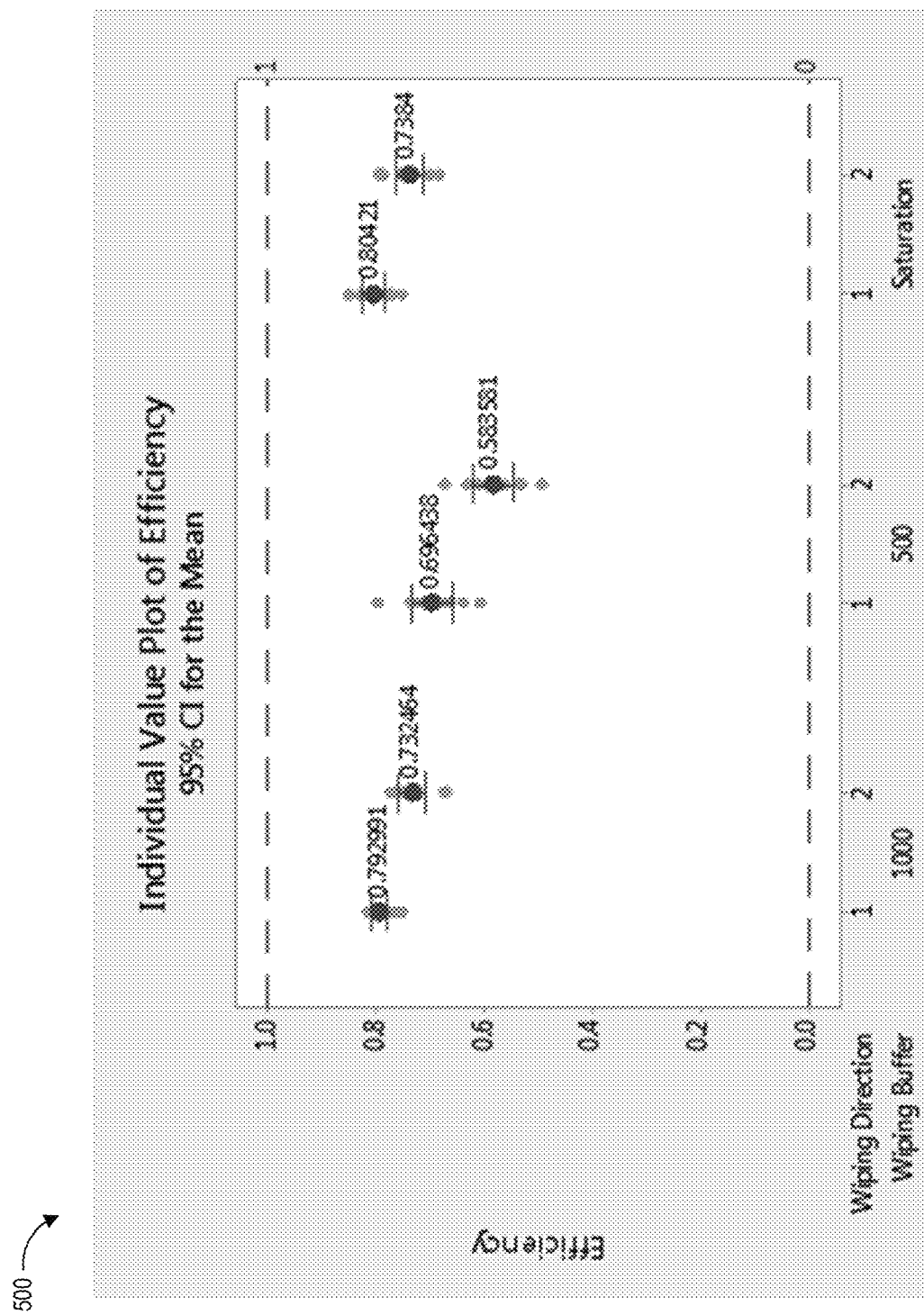
FIG. 5 depicts a plot of data correlating combinations of collection swab wiping direction and volume of wiping buffer with pickup efficiency according to the example swabbing procedure.

FIG. 5 depicts a plot 500 of data correlating combinations of collection swab wiping direction and volume of wiping buffer with pickup efficiency according to the example swabbing procedure. Through extensive testing and analysis, it was discovered that stroke direction during the sampling procedure has a significant effect on pickup efficiency (and therefore on the accuracy of the test result). As described above, existing antineoplastic swabbing methods instruct the user to first swab the test area in a first direction using a cotton tipped swab stick, and to then swab the same area in a second direction perpendicular to the first direction. Direction as used herein can refer to the orientation of the swab stroke relative to the test area or user location, and a user can swab in strokes back and forth along a specific direction (e.g., horizontally or vertically relative to the test area/user location). Existing methods are based upon the assumption that wiping the surface twice results in better pickup efficiency because the cotton tipped swab stick passes over the same surface area twice.

Unexpectedly, the results of the presently disclosed testing revealed that swab strokes along a single direction/orientation result in a higher pickup efficiency than two sets of swab strokes along two perpendicular directions. The plot 500 illustrates these unexpected findings, with the pickup efficiency percentage (ranging from 0.0=0% to 1.0=100%) along its vertical axis and various combinations of wiping direction protocols (with 1 representing a wiping direction protocol of swabbing along a single orientation and 2 representing a wiping direction protocol of swabbing along two perpendicular orientations) and wiping buffer (measured in microliters) along its horizontal axis. As shown by the adjacent pairs of data for sampling performed using the same volume of buffer solution but with different swabbing direction protocols, pickup efficiency decreased as the surface was wiped the second time in the perpendicular direction, contrary to the assumptions of previous testing protocols. Accordingly, another sampling protocol according to the present disclosure can be a directional protocol that instructs the user to select a direction for the stroke orientation (e.g., horizontal or vertical relative to the test area and/or user location) and then swab using strokes only along that selected direction.

Other factors that may influence pickup efficiency and thus may be the subject of other sampling protocols as described herein include the amount of overlap between wiping rows, wiping with the same leading edge of the swab or not, whether the wiping was performed with or against (perpendicular to) the brushed grain direction on a stainless steel surface, and wiping direction coincident with or perpendicular to the swab fabric weave direction. In some embodiments, such factors may have a less significant impact on pickup efficiency than speed, force, and wiping direction, and thus kits according to the present disclosure may omit instructions for use or protocols relating to these factors.

Figure 6A:
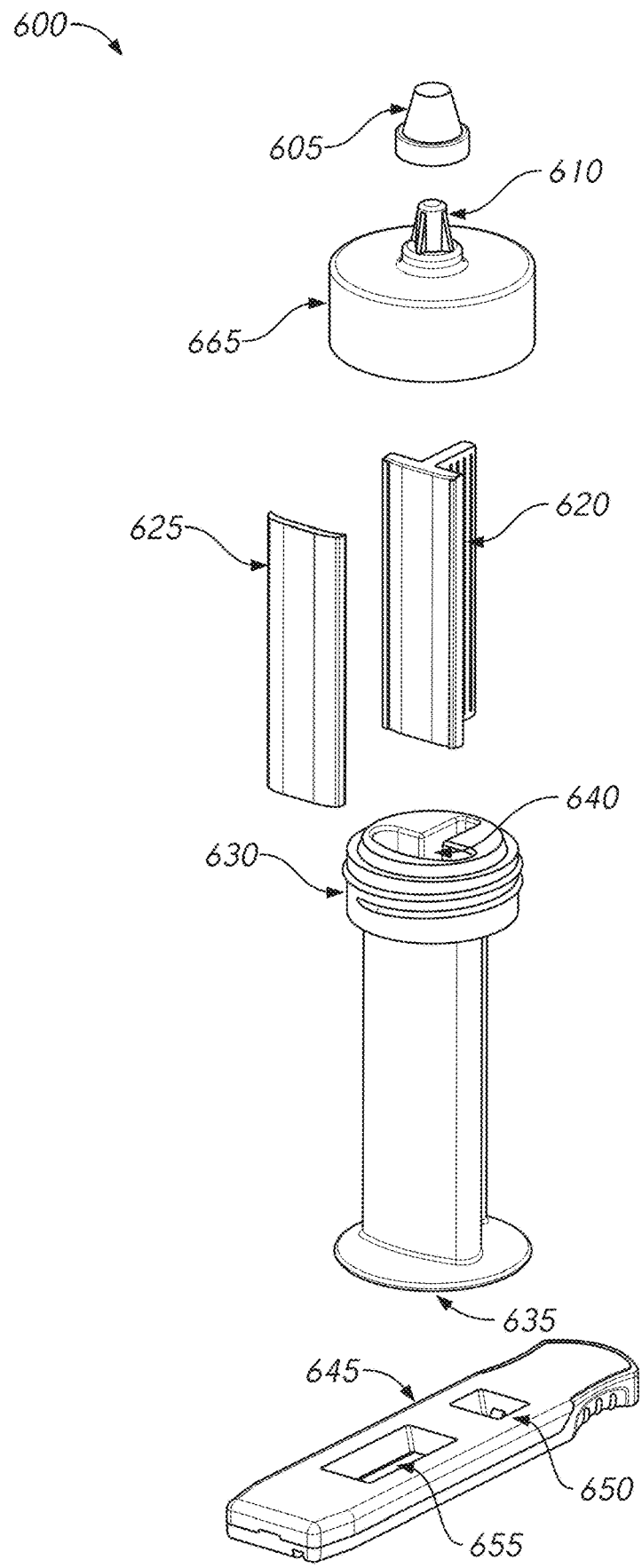
FIGS. 6A-6C illustrate an example of a contaminant collection device and detection assay that can be used in embodiments of the disclosed techniques.
Figure 6B:
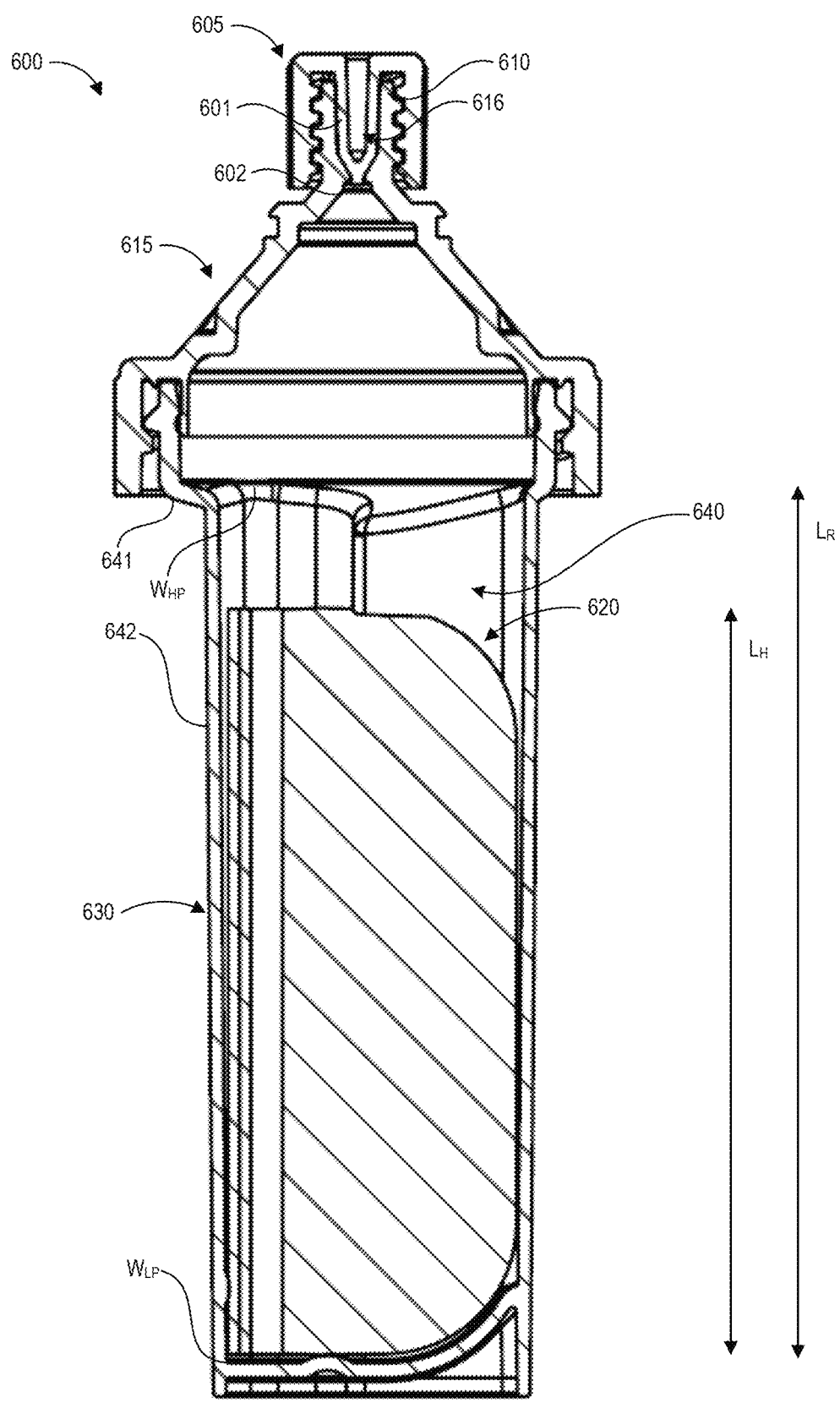
Figure 6C:
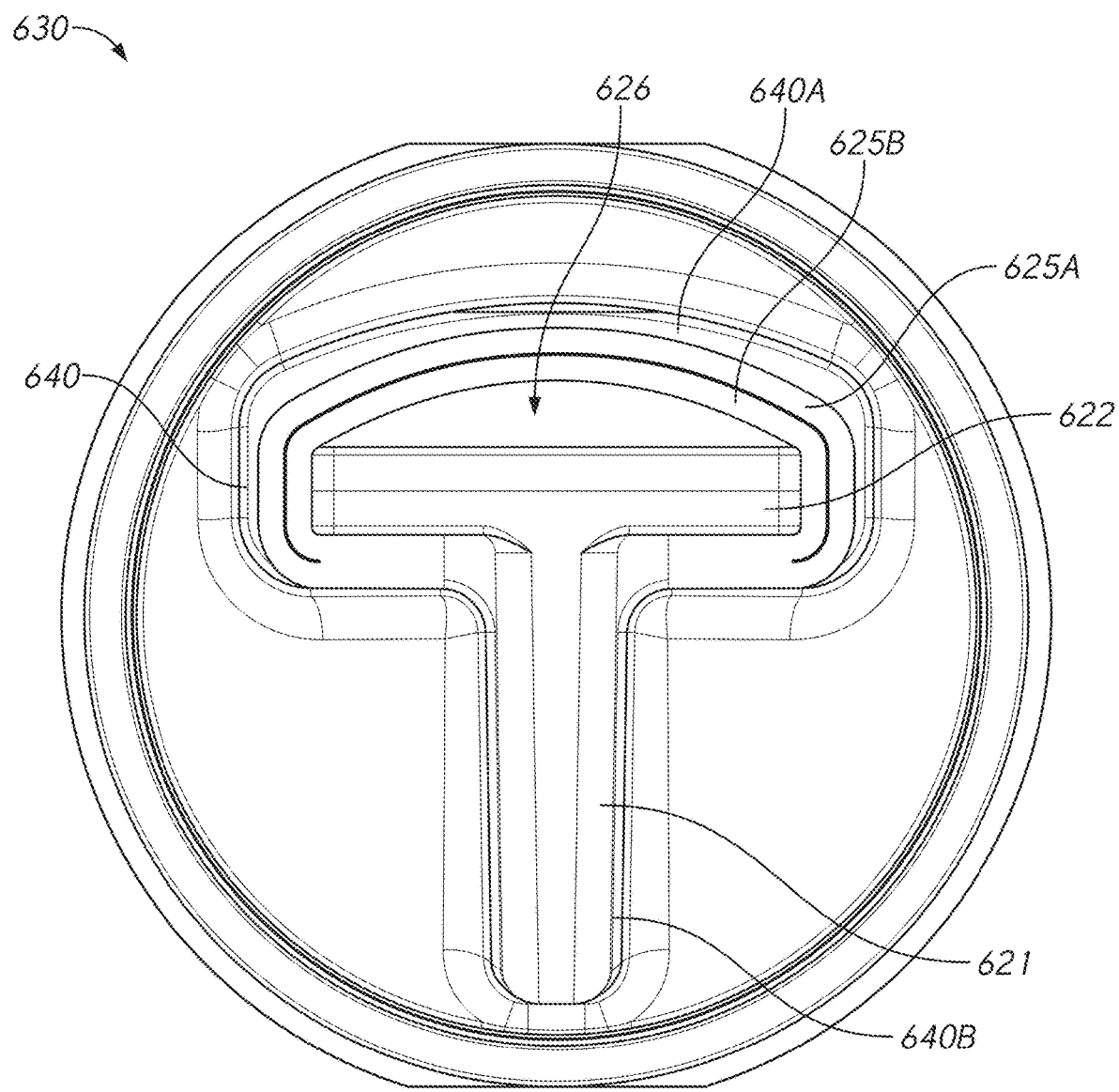

The second efficiency term of the formula described above relates to shedding efficiency, or the ability to extract collected contaminants from the swab material for testing. FIGS. 6A-6C illustrate an example of a contaminant collection device and detection device that can be used in embodiments of the disclosed techniques to extract the collected contaminants from the swab fabric into a buffer solution that can be used in a detection assay. FIG. 6A illustrates an example of a contaminant collection device 600 and an assay detection device 645, which may be the components referenced at steps 101, 104, 106, 107, 108, and 109 of FIG. 1A. In this example, detection device 645 is a test strip 645 that includes a lateral flow assay. The collection device 600 can include a container 630, a handle 620 with a swab 625, a removable top 615, and a removable cap 605. In some examples, components of the collection device 600 are packaged separately. For example the collection device 600 can include a first package and a second package. The first package includes a buffer-filled container 630 in sealed assembly with a removable top 615 and a removable cap 605. The second package includes a handle 620 and a swab 625 that has been pre-moistened with buffer fluid. The first package and the second package can be individually sealed (in some cases, hermetically sealed) and can be provided to the user in a kit described in greater detail below.

The container 630 can be liquid-tight when the container 630, removable top 615, and removable cap 605 are coupled together, and can contain buffer fluid. The removable top 615 and container 630 can include threads for reversible engagement as illustrated, or can include other suitable fluid-tight coupling structures, for example a snap fit. The container 630 can include a stability foot 635 to keep it oriented upright when positioned on a flat surface. The cap 605 can be threaded or configured to securely snap onto the nozzle 610 of the removable top 615. The removable top 615 can be removed to provide access to the well 640 of the container 630, allowing a user to, for example, insert the handle 620 and swab 625 into the container 630. The removable top 615 also allows a user to pour fluid from the container 630 onto a test surface. In other embodiments in which the user uses the container 630 with a pre-moistened swab 625, the user may not pour any fluid from the container 630, thereby maintaining a known volume of fluid in the container 630. This feature can be beneficial for accurate assessment of collected contaminant concentration.

The handle 620 can be the handle 200A described with reference to FIG. 2A above. The handle 620 can have a "T-shaped" cross section with the "top" of the T securing the swab 625 and the "downwardly-extending" portion of the T used as a grip portion. The size of the handle 620 can be selected to minimize the total volume of the handle 620 while still providing a grip portion of sufficient size to prevent contact between the hand of the user and the test surface.

The swab 625 can be constructed from a specialized material having desired pickup efficiency and shedding efficiency for detecting trace amounts of contaminants. In one example implementation, the swab 625 includes one or more layers of woven polyester fibers. Though shown in exploded view to illustrate the various components, the swab 625 can be coupled to the handle 620, thereby providing the user with a mechanism to wipe a test surface without contacting the surface and buffer fluid. The swab 625 and handle 620 can be coupled, for example by ultrasonic welding to melt material of the handle 620 into portions of the swab material, a clamping mechanism built into the handle 620, by adhesive, or by any other suitable attachment mechanism. There may be one or multiple layers of swab material provided on the handle 620. The swab material may be attached to the handle 620 in a taut manner or may be loosely attached to the handle 620. The swab 625 can include two layers of fabric. In one advantageous embodiment described in detail below, the swab is attached to the handle 620 in a configuration where portions of the swab material that are not directly fastened to the handle 620 remain loose relative to the handle 620.

The well 640 of the container 630 can be shaped to substantially conform to the outer dimensions of the coupled handle 620 and swab 625 in some embodiments, so that the swab 625 and handle 620 can be securely fitted within the well 640. In the illustrated example, the well 640 has a "T-shaped" cross section that fits the profile of the handle 620 and swab 625. This shape of the container can minimize the volume of buffer fluid needed to submerse a given portion of the handle in the buffer fluid. It is also shaped to minimize the buffer fluid that can reside around the grip portion of the "T" of the handle, thereby ensuring that most of the buffer fluid will be in the portion of the well 640 where the swab 625 is located. The shape of the well 640 is designed such that most of the fluid volume will be around the swab 625 and the container/handle design may not allow the swab 625 to be compressed against the inside wall of the container 630, for example by providing additional space in the well 640 around the swab 625.

In some embodiments, the well 640 of the container 630 can be up to two times longer than the handle 620. This allows the handle 620 to slide back and forth with the buffer fluid as the container 630 is inverted. This movement may aid in better flushing of the fluid through the swab 625.

Though not illustrated, the container 630 can contain a certain volume of a buffer solution which will help lift the analyte of interest (in this non-limiting example, a contaminant) from the swab material, keep the contaminate stable until it is ready to be transferred to the test strip 645, and provide a fluid suitable for transferring the contaminant to the test strip and for cooperating with the capillary action of the test strip to carry the contaminant to reaction zone(s) on the test strip. In some embodiments the container 630 can include buffer solution suitable for wetting a determined test area, for example corresponding to an area template or area instructions provided with the kit. A user can pour buffer solution from the container 630 onto the test surface and then wipe the test surface with swab 625. In some embodiments at least some of the buffer solution can be provided in a separate container, for example packaging of the swab 625. After being applied to the test surface, the buffer solution can be absorbed, together with any contaminants contained therein, by the material of the swab 625.

As described herein, in some embodiments no buffer solution may be poured from the container 630, and instead the swab material 625 can be pre-moistened with the buffer solution (or a dilute version of the buffer solution). The swab 625 can be provided separately in a sealed package to maintain its pre-moistened state. A user can remove the swab 625 and handle 620 and wet the test surface by wiping the swab 625 across the test surface, such as by applying force to release the buffer solution from the pre-wetted swab 625. The user can in some embodiments perform additional wiping of the test surface with the swab 625 after release of the buffer solution, for example until most or all of the buffer solution is re-absorbed into the swab 625.

After completing wiping of the test area of the test surface, the user can insert the handle 620 and swab 625 into the container 630 and couple the removable top 615 and removable cap 605 with the container 630 to enclose the buffer fluid within the fluid-tight well 640. This configuration is shown in more detail in FIGS. 6B and 6C. The user can agitate the swab 625 within the sealed container 630 to shed collected particles from the swab material into the buffer solution, as described in more detail with respect to FIG. 6D. To transfer fluid from the well 640 to the test strip 645, the user can remove the cap 605 and expel fluid through the nozzle 610, for example by inverting the container 630 and allowing fluid to drip through nozzle 610. The nozzle 610 can be sized for controlled release of a drop (or other volume) onto the test strip 645.

Test strip 645 can include a sample receiving zone 650 and reaction zone 655. The user can transfer the fluid from container 630 to sample receiving zone 650, and the test strip can wick the fluid and any contaminants contained therein along the length of the test strip to and/or through the reaction zone 655. Reaction zone 655 can include one or more analyte binding regions. As illustrated, the actual capillary test strip can be housed within a cartridge with windows corresponding to the locations of the sample receiving zone 650 and reaction zone 655.

FIG. 6B illustrates a cutaway side view of the collection container 630 of FIG. 6A in a sealed configuration. In the sealed configuration, the handle 620 positioned within the collection container 630 with the removable top 615 and sealing the interior of the container 630. FIG. 6B shows the rim 641 forming a cylindrical opening leading into the T-shaped well 640. As illustrated, in this non-limiting embodiment the length $L_H$ of the handle 620 is less than the length $L_R$ of the interior of the well 640 that extends from the highest point of the well $W_{HP}$ to the lowest point of the well $W_{LP}$. In some embodiments, the difference between the length $L_H$ of the handle 620 and the length $L_R$ of the interior of the well 640 can be at least ⅛th inches, and preferably between ⅛th inches and ¼ inches. In one example implementation, the length $L_H$ of the handle 620 is about 2 inches and the length $L_R$ of the interior of the well 640 is about 2.25 inches. Providing a well with a greater length than the handle advantageously increases the amount of contaminant flushed from the surface of the swab material, for example when the user inverts container 630 and buffer fluid in the container 630 washes back and forth across the swab material to remove any picked-up contaminants. While the user inverts the container, the handle 620 slides back and forth within the well 640 to provide for better washing of the fabric than in implementations having the same length for the handle and the well.

FIG. 6B also illustrates a cross-sectional view of how the removable cap 605 of the collection device of FIG. 1A secures onto the threaded nozzle 610 of the top 615. The removable cap 605 includes a protrusion 601 extending into the channel 616 of the nozzle 610 of the removable top 615. The protrusion 601 is configured to plug the channel 616 of the nozzle 610 of the top 615, and can be tapered to match the tapered contours of the channel 616. The protrusion 601 has at its lowest region (e.g., the region positioned furthest within the channel 616 when the cap 605 is screwed onto the nozzle 610) a post 602 that extends into the inner aperture 616A of the channel 616. This shaping of the cap 605 can serve to minimize any "dead space" in the channel 616 of the top 615 that could collect buffer solution in a manner that interferes with test result accuracy. For example, without the described features of the cap 605, buffer solution could collect within the channel 616 of the top 615 and stay in the channel 616 as the swab material 620 is agitated to release collected contaminants. This "trapped" buffer would be the first liquid to drip out of the container 630 due to its positioning in the channel 616, but it may not have mixed with the rest of the solution during agitation and thus would not contain any (or a significant quantity of) collected contaminants.

Additional features of the cap 605 according to the present disclosure advantageously avoid these potential issues. For example, the protrusion 601 of the cap 605 has an exterior shape that corresponds to the inner shape of the channel 616, thereby preventing buffer solution from accumulating within the channel 616 of the top 615. The post 602 is sized to fill the innermost aperture of the channel 616 without interference, and the post 602 and engaged surfaces of the channel 616 cooperate to prevent fluid from entering the channel 616 when the cap 605 is fully screwed onto the nozzle 610 of the top 615.

FIG. 6C illustrates a top view of the handle 620 positioned within the well 640, and depicts a representation of the swab material 625 (shown in two layers 625A, 625B) secured to the handle. As illustrated, the swab material 625 can be secured loosely to the base portion 622 of the handle 620 such that there can be a gap between the inner layer 625B of swab material and the surface of the base portion 622 facing the inner layer 625B. For example, the swab material 625 can be between 0.050 inches and 0.220 inches longer than the width of the handle. This results in portions of the fabric remaining loose relative to the base portion 622 of the handle 620 and forming a gap 626 between the swab material and the handle 620 in which buffer fluid can freely flow, thereby allowing fluid to efficiently pass through and agitate the portion of the swab material that made direct contact with the test surface. The layers 625A, 625B can have the same or different widths across the width of the base portion 622.

The well 640 includes a first portion 640A sized to receive the base portion 622 of the handle 620 with the swab material 625, and the well further includes a second portion 640B sized to receive the grip portion 621 of the handle 620.

In examples such as that illustrated in FIG. 6C, the second portion 640B is sized to snugly receive the grip portion 621 of the handle 620 (in other words, there is very little space between the second portion 640B and the grip portion 621 such that their surfaces are in constant contact or near constant contact). As illustrated, the second portion 640B has a substantially similar cross-section to the grip portion 621, where "substantially" refers to a cross-section of the second portion 640B being slightly larger to allow the grip portion 621 to slide into the second portion 640B. The cross-section of the first portion 640A corresponds to the cross-sectional area occupied by the base portion 622 of the handle 620 with the swab material 625 with a small gap to allow the swab material 625 to flow freely in the buffer solution in the well 640. Beneficially, providing the second portion 640B to have a similar interior volume to the volume occupied by the grip portion 621 causes the grip portion 621 to push most if not substantially all fluid in the well 640 out of the second portion 640B and into the first portion 640A when the handle 620 is inserted into the container. This can reduce the amount of buffer solution required to be placed in the well 640 in order to wash the desired amount of contaminants from the swab material 625, which beneficially increases the concentration of the contaminants in the solution compared to other embodiments that require greater amounts of buffer solution. The first portion 640A can be sized to substantially match the shape of the handle's base portion 622 with swab material attached, though the first portion 640A can (as illustrated) be slightly larger in order to facilitate agitation of the loose swab material during inversion of the container 630.

As such, the complementary shapes of the well 640 and handle 620 (including swab material 625) provide at least the following benefits: (1) minimizing unneeded "dead space" (e.g., space not occupied by handle 620 or swab material 625) inside the well 640 when the handle is inserted into the well 640, thus reducing the volume of buffer solution needed to extract contaminants from the swab material; and (2) maximizing concentration of the contaminant in the solution by promoting agitation of the material to extract the contaminant. Regarding unneeded "dead space" and the first portion 640A, a small amount of space is beneficial around the swab material 625 in order to allow the swab material to flow within the buffer solution and be agitated by turbulence during container inversions, thereby releasing the maximum quantity of collected contaminant from the swab material 625 into the solution. However, providing too much dead space creates a requirement for a greater amount of buffer solution to contact the swab material 625, thereby reducing the concentration of collected contaminant in the buffer solution. The complementary shapes of the well 640 and handle 620 thus enable accurate detection of even minute quantities of collected contaminants by maximizing both contaminant shedding from the swab material 625 and contaminant concentration in the buffer solution.

Although the sides of the grip portion 621 and second portion 640B of the well 640 are depicted as being straight, in other embodiments the sides of the grip portion 621 and the inner walls of the second portion 640B of the well 640 can be "keyed," that is, have corresponding features (e.g., curved or angled portions). Embodiments having a keyed grip portion 621 and second portion 640B beneficially can maintain the positioning of the grip portion 621 fully within the second portion 640B rather than allowing the base portion 622 to slide toward the far side of the first portion 640A of the well.

Example Inversion Protocol

Figure 6D:
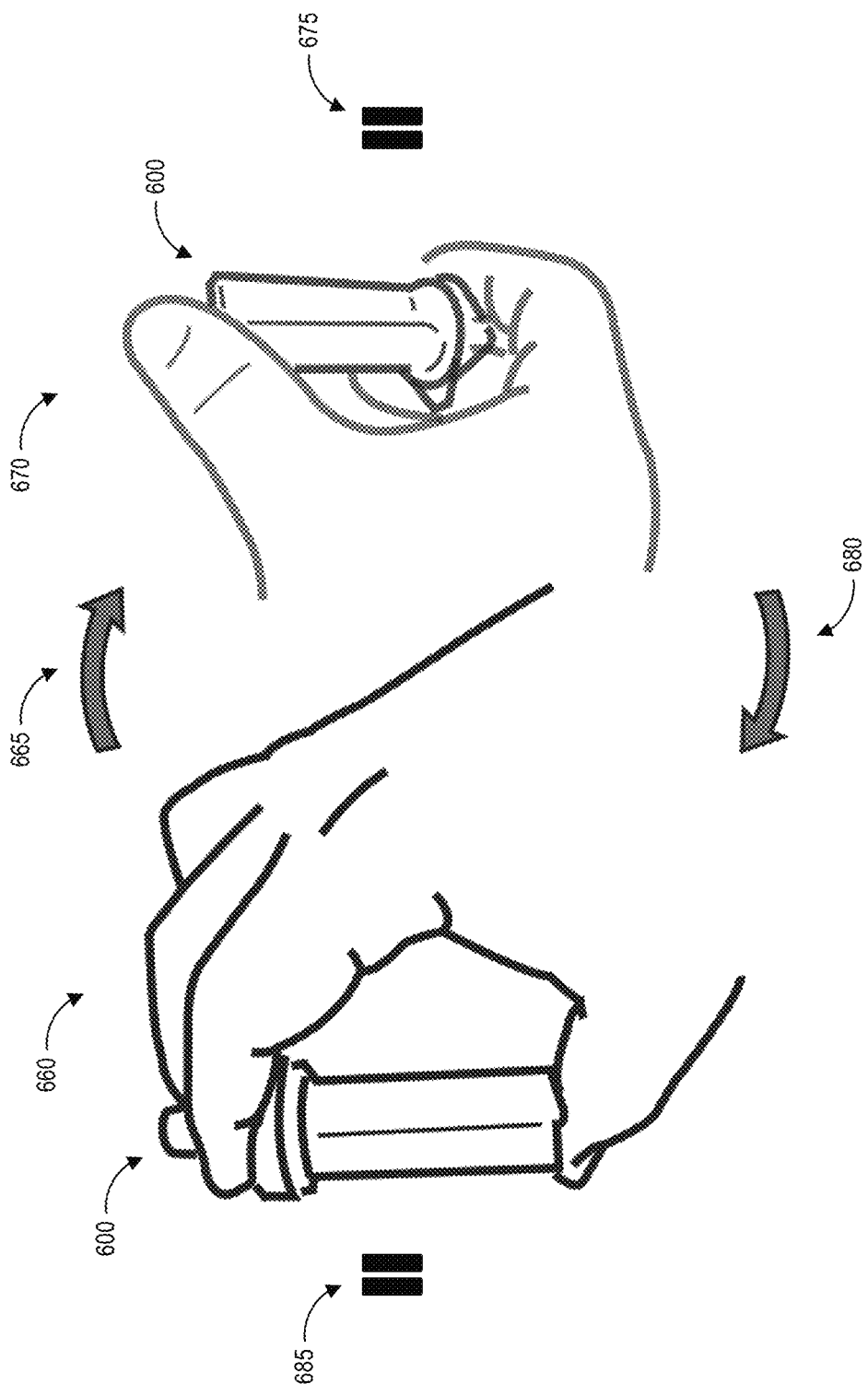
FIG. 6D illustrates an example inversion protocol for the collection device of FIGS. 6A-6C.

Inversion protocols and techniques that reliably and consistently extract the collected analyte of interest (such as molecules of contaminant) from the swab fabric into a solution that can be used in a detection assay will now be described. FIG. 6D illustrates example graphical steps of an inversion protocol 600 for the collection device of FIGS. 6A-6C that can achieve heightened reliability and consistency for such extraction efficiency. FIG. 6D may be performed for example as step 104 of the process 100A. Prior to performing inversions according to the protocol shown in FIG. 6D, the user places the swab material 625 and handle 620 assembly into the well 640 of the container 630 containing a buffer solution. As described above, the well 640 in this implementation is specifically designed to match the shape of the handle assembly as closely as possible (while still allowing room for agitation of the swab material 625). Matching the shape reduces the amount of the buffer solution that is required to extract collected molecules from the swab material 625 because this only leaves room for the solution to flow through the area occupied by the swab material 625. It will be understood that other well/handle assembly configurations are suitable for use with the inversion protocol 600, and will still yield high extraction efficiencies for the collected particles. The user seals the handle assembly inside the well using the removable top 115 and cap 105.

The sealed container 600 is then turned upside down and rightside up a number of times, each individual upside down and rightside up movement referred to herein as an inversion. Inverting the container allows the enclosed solution to flow back and forth across the swab material 625, thereby mixing with the solution that pre-wetted the swab material and with molecules the swab material 625 has retained during the swabbing procedure. The swab material 625 and handle 620 also move back and forth in the container as it is inverted, which adds to the washing and mixing action that agitates the swab material 625 and assists with extraction. As shown in FIG. 6B, the container well 640 is longer than the swab and handle to permit this movement.

For example, according to an inversion protocol as described herein, the user can begin by holding the sealed container 600 upright as shown in upright configuration 660. The user can then perform an inversion 665 to rotate the container 600 into the inverted configuration 670. The user can pause 675 in the inverted configuration 670 for some predetermined duration before performing another inversion 680 to return the container 600 back to the upright configuration 660. The user can again pause 685 before performing the next inversion 665, and can cycle through the configurations 660, 670 each a specified number of times.

The user can pause 675 in the inverted configuration 670 for a half second, one second, several seconds, or another suitable amount of time. The extraction efficiency can be higher if the inversion cycle is paused at each half cycle to allow the contents to settle. In some examples, as explained above, the user can additionally pause 685 at the end of each complete cycle. The pause 685 can last for a half second, one second, several seconds, or another suitable amount of time.

In some embodiments, the container can be rotated 180 degrees during inversions 665, 680. The extraction efficiency can be higher in some embodiments if the sealed container 600 is fully inverted 180° from upright than if the sealed container 600 is rotated some angle less than 180°. This can be true even if the handle still moves from end to end within the container.

In some non-limiting examples, the speed with which the user performs the inversions 665, 680 can have very little (or in some cases, no measurably significant) effect on extraction efficiency. The inversion protocol according to the present disclosure can nonetheless instruct the user to perform the inversions at a rate that will minimize or prevent the solution inside from creating foam. This instruction can be particularly beneficial for example systems in which the solution includes a small amount of detergent that will foam if agitated too quickly.

One inversion protocol can call for fully inverting the container 180° and back again five times at a rate of about one second per half cycle (e.g., one second per inversion). This protocol can additionally specify that the user should pause the movement for about one second at the end of each half cycle (e.g., at each upright position 660 or fully inverted position 670) before rotating it to the other position. This can allow the contents to settle between successive inversions, which may aid in increasing and/or reducing variation in extraction efficiency.

Figure 7A:
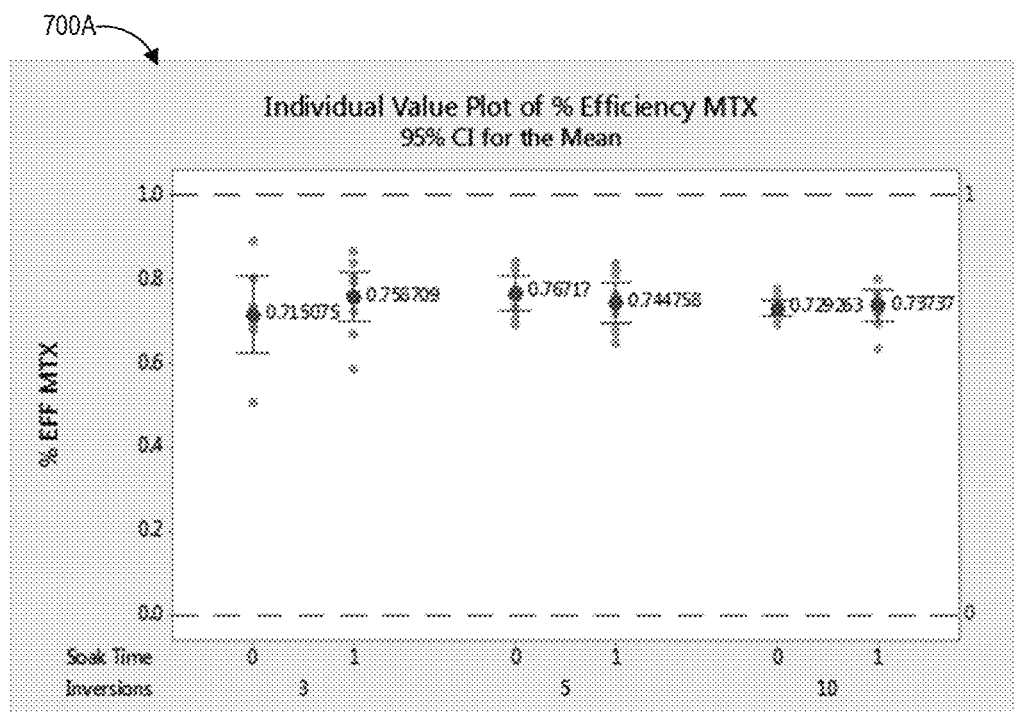
FIGS. 7A and 7B depict plots of data correlating the soak time and number of inversions of various inversion protocols with shedding efficiency according to one example inversion procedure.
Figure 7B:
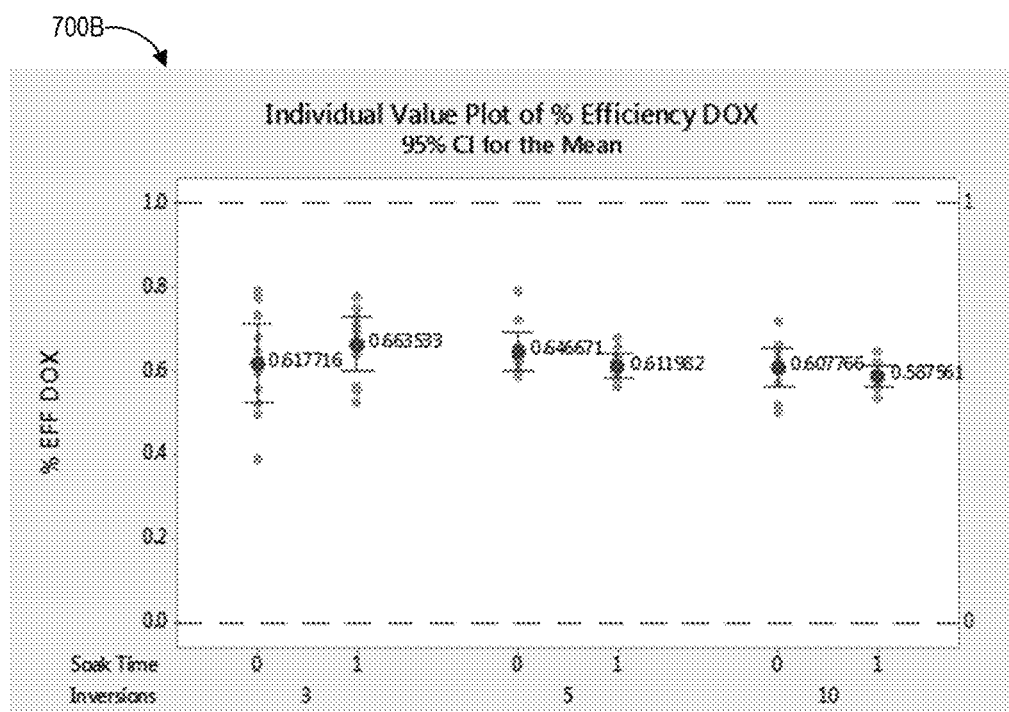

FIGS. 7A and 7B depict plots 700A, 700B of data correlating the soak time and number of inversions of various inversion protocols with shedding efficiency according to an example inversion procedure. As shown in the plots 700A, 700B, the number of inversion cycles was tested at 3, 5 and 10 cycles. The testing revealed that they were all statically equal in extraction performance (represented by the circles in the intervals) but the variation was higher with only 3 cycles (with variation shown by the span of the interval). Five cycles provided the optimum performance with minimal fatigue to the user.

The plot 700A of FIG. 7A shows extraction efficiency percentage (ranging from 0.0=0% to 1.0=100%) for Methotrexate along its vertical axis and various combinations of soak time protocols (with 0 representing a soak time protocol that does not allowing the swab to soak in the buffer solution in the container prior to the agitation, and 1 representing a soak time protocol that requires allowing the swab to soak in the buffer solution in the container prior to the agitation) and inversion cycle numbers along its horizontal axis. As shown by the adjacent pairs of data for sampling performed using the same number of inversion cycles but with different soak time protocols, extraction efficiency tended to increase when the protocol includes pausing at half cycles for three inversion cycles.

The plot 700B of FIG. 7B shows extraction efficiency percentage (ranging from 0.0=0% to 1.0=100%) for Doxorubicin along its vertical axis and various combinations of soak time protocols (with 0 representing a soak time protocol that does not require allowing the swab to soak in the buffer solution in the container prior to the agitation, and 1 representing a soak time protocol that requires allowing the swab to soak in the buffer solution in the container prior to the agitation) and inversion cycle numbers along its horizontal axis. As shown by the adjacent pairs of data for sampling performed using the same number of inversion cycles but with different soak time protocols, extraction efficiency tended to increase when the protocol includes pausing at half cycles for three inversion cycles.

In the plots 700A, 700B, the small dots represent actual data points. The large dot within each group represents the estimated mean (average) of the actual data points. The brackets around each group indicate the statistical range in which the man could actually be located to a 95% confidence level, based on the sample size and variation of the actual data points. If the brackets overlap between two groups, this indicates that the two groups may not be statistically distinguished from one another. One takeaway from the plots 700A, 700B is that there may be no statistical difference between mean efficiency due to the number of inversions, but the amount of variation (the spread of the grey dots or the length of the blue brackets) was observed to increase as the number of inversions decreases. Some implementations may seek to decrease the variation if the mean efficiencies are equal.

Orientation of the swab in the container may have a significant effect on extraction efficiency. In some early tested sampling cases, the extraction efficiency performed better if the swab was facing up as the container was inverted than if it faced down. "Up" as used here refers to when the swab is on top (the handle is on the bottom) as the container passes through the horizontal position as it is being inverted. "Down" as used here refers to when the swab in on the bottom (and the handle is up) as the container passes through the horizontal position as it is being inverted. Accordingly, in some embodiments, sampling protocol may specify a specific orientation for inserting the handle into the container well. This effect, however, was reduced to a minimal impact on efficiency in further testing as other aspects of the design and process were improved. Accordingly, in some embodiments sampling protocol may not specify any orientation for inserting the handle into the container well.

Figure 8:
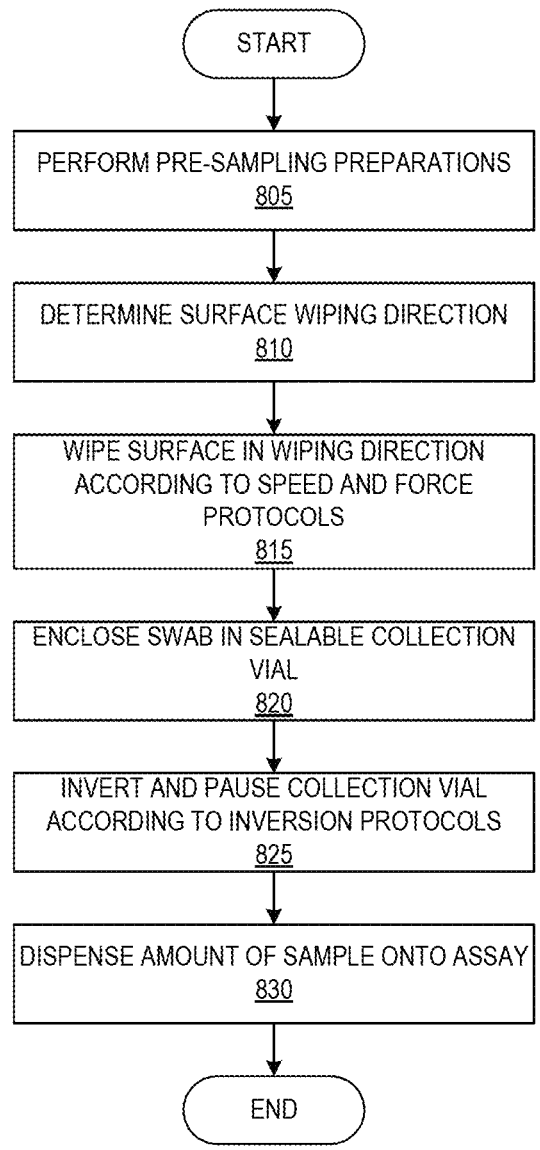
FIG. 8 depicts an example process for contaminant sample collection according to the present disclosure.

FIG. 8 depicts an example contaminant sample collection process 800 according to the present disclosure. The process 800 can be performed as an embodiment of the process 100A using the disclosed sampling protocols. Some embodiments of the process 800 can include providing the user with automated sensing of swabbing parameters for real-time feedback on compliance with swabbing protocols and/or automated tracking of user compliance with swabbing protocols, for example via a swab with embedded sensors or an augmented reality device observing the sampling techniques. Some embodiments may instead provide a lower cost swab without any computing capabilities and can provide graphical or textual instructions for the user to monitor their own compliance with the sampling protocol.

At block 805, a user can perform pre-sampling preparations, for example as described above with respect to blocks 101 and 102 of process 100A. Block 805 can include putting on protective sterile gloves, removing a pre-moistened swab from a first sealed package, removing a collection vial from a second sealed package, opening the removable top of the collection vial while leaving the cap coupled to the nozzle of the removable top, and placing a template on the test surface.

At block 810, the sampling protocol can instruct the user to select a direction for wipe strokes. For example, as shown in block 103 of process 100A and in FIG. 2B, the stroke direction can be vertical relative to the demarcated test area. In other embodiments the stroke direction can be perpendicular to that shown in block 103 of process 100A and in FIG. 2B, in other words horizontal relative to the demarcated test area.

At block 815, the sampling protocol can instruct the user to wipe the test surface according to the determined wiping direction and in accordance with speed and force protocols. In one non-limiting example, as described above a speed protocol can instruct the user to complete a 12 inch swab stroke within 3 seconds, or to use a maximum swab speed of 50 mm/s or 100 mm/s. As described above, a force protocol according to the present disclosure can instruct the user to apply the swab onto the test surface using at least 2 pounds of force, at least 5 pounds of force, or within a certain range of 2 pounds and 5 pounds of force.

At block 820, the user can complete swabbing the entire demarcated test area and enclose the swab handle in the collection vial. For example, the user can place the swab handle assembly into a correspondingly-shaped well of the collection vial and seal the removable top onto the collection vial, thereby enclosing the swab handle assembly inside the collection vial. The cap may remain in place sealing the removable top nozzle, thus creating an enclosed space that beneficially seals away any picked-up hazardous contaminants from the user, preventing spread of contamination. Block 820 can be performed between block 103 and block 104 in some embodiments.

At block 825, the user can invert the collection vial a number of times, and optionally pause movement of the collection vial during the inversions, according to a specified inversion protocol in accordance with the present disclosure. As described above, the inversion protocol can instruct the user to fully invert the container 180° and back again five times at a rate of about one second per half cycle (for an inversion process totaling 10 seconds). This protocol can optionally specify that the user should pause the movement for about one second at the end of each half cycle before rotating it to the other position (for a total inversion process totaling 20 seconds), or at the end of each cycle (for a total inversion process totaling 15 seconds). Block 825 can be performed as block 104 in some embodiments, and can use an inversion protocol as described with reference to FIG. 6D.

At block 830, the user can remove the cap from the removable top, exposing the channel through its nozzle. The user can dispense an amount (e.g., four drops or another suitable quantity) of the sample onto a test assay or other test device. Block 830 can be performed as block 106 in some embodiments. The process 800 can then loop through similar blocks as blocks 107, 108, and 109 of the process 100A for determining a test result based on the collected sample. By providing the sampling protocols discussed with respect to process 800, a hazardous contaminant sampling procedure according to the present disclosure can produce higher pickup and extraction efficiencies than less constrained sampling techniques, thereby yielding more accurate test results based on the collected samples.

Implementing Systems and Terminology

Implementations disclosed herein provide systems, methods and apparatus for detection of the presence and/or quantity of hazardous drugs. One skilled in the art will recognize that these embodiments may be implemented in hardware or a combination of hardware and software and/or firmware.

The assay and template reading functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like. The phrase "based on" can mean "based only on" and "based at least on," unless expressly specified otherwise.

The previous description of the disclosed implementations is provided to enable any person skilled in the art to make or use the present disclosure. Various modifications to these implementations will be readily apparent to those skilled in the art, and the generic principles defined herein may be applied to other implementations without departing from the scope of the present disclosure. Thus, the present disclosure is not intended to be limited to the implementations shown herein but is to be accorded the widest scope consistent with the principles and novel features disclosed herein.

What is claimed is:

1. A method of collecting a sample of a hazardous contaminant from a test surface, the method comprising:
obtaining a collection device comprising a handle coupled to an absorbent swab material;
demarcating a test area on the test surface by adhering to the test surface a template having alignment markers thereon; and
wiping the test area with the absorbent swab material according to a specified swabbing protocol and based at least in part on the alignment markers, wherein according to the swabbing protocol the wiping includes maintaining at least a two pound force on the absorbent swab material as it contacts the test surface.

2. The method of claim 1, wherein according to the swabbing protocol the wiping includes maintaining at least a five pound force on the absorbent swab material as it contacts the test surface.

3. The method of claim 1, further comprising applying the at least two pound force on the absorbent swab material via the handle.

4. The method of claim 1, wherein the wiping comprises sliding the absorbent swab material along the test surface in a plurality of strokes, each stroke spanning a first dimension of the test area and the plurality of strokes collectively spanning a second dimension of the test area perpendicular to the first dimension.

5. The method of claim 4, wherein according to the swabbing protocol each stroke is performed for a known amount of time.

6. The method of claim 4, wherein according to the swabbing protocol each stroke is performed at a speed less than or equal to a known speed.

7. The method of claim 4, wherein according to the swabbing protocol each of the plurality of strokes is oriented in a parallel direction.

8. The method of claim 1, wherein the collection device comprises a sealable vial having an interior well shaped to substantially match a cross-section of the handle, the method further comprising:
inserting the handle and absorbent swab material into the interior well;
sealing the vial; and
agitating the absorbent swab material by inverting the vial according to a specified inversion protocol.

9. The method of claim 8, wherein according to the inversion protocol the agitating comprises performing a specified number of cycles, each cycle comprising:
holding the vial in a first configuration;
inverting the vial approximately 180 degrees into a second configuration;
pausing movement of the vial for a specified amount of time; and
returning the vial to the first configuration.

10. The method of claim 9, further comprising:
removing a cap of the sealable vial;
dispensing at least a portion of the sample onto an assay; and
determining a test result based on the assay, the test result representing a presence or concentration amount of the hazardous contaminant on the test surface.

11. A method of collecting a sample of a hazardous contaminant from a test surface, the method comprising:
obtaining a collection device comprising a handle coupled to an absorbent swab material;
demarcating a test area on the test surface by adhering to the test surface a template having alignment markers thereon; and
wiping the test area with the absorbent swab material according to a specified swabbing protocol and based at least in part on the alignment markers, wherein according to the swabbing protocol movement of the handle during the wiping does not exceed a speed of 100 millimeters per second.

12. The method of claim 11, wherein the wiping does not exceed a speed of 50 millimeters per second.

13. The method of claim 11, wherein, according to the swabbing protocol, movement of the handle during the wiping further comprises applying at least a two pound force on the absorbent swab material via the handle.

14. The method of claim 11, wherein the wiping comprises sliding the absorbent swab material along the test surface in a plurality of strokes, each stroke spanning a first dimension of the test area and the plurality of strokes collectively spanning a second dimension of the test area that is perpendicular to the first dimension.

15. The method of claim 14, wherein according to the swabbing protocol each of the plurality of strokes is oriented along a common orientation.

16. The method of claim 11, wherein the collection device comprises a sealable vial having an interior well shaped to substantially match a cross-section of the handle, the method further comprising:
inserting the handle and absorbent swab material into the interior well;
sealing the vial; and
agitating the absorbent swab material by inverting the vial according to a specified inversion protocol.

17. The method of claim 16, wherein, according to the inversion protocol, the agitating comprises performing a specified number of cycles, each cycle comprising:
holding the vial in a first configuration;
inverting the vial approximately 180 degrees into a second configuration;
pausing movement of the vial for a specified amount of time; and
returning the vial to the first configuration.

18. The method of claim 17, further comprising:
removing a cap of the sealable vial;
dispensing at least a portion of the sample onto an assay; and
determining a test result based on the assay, the test result representing a presence or concentration amount of the hazardous contaminant on the test surface.

19. A method of extracting a sample of a hazardous contaminant from an absorbent swab material, the method comprising:
inserting a handle coupled to the absorbent swab material into a sealable vial having an interior well comprising a first portion and second portion shaped to substantially match a cross-section of a grip portion and a base portion of the handle after wiping a test surface with the absorbent swab material according to a specified swabbing protocol;
sealing the vial; and
agitating the absorbent swab material by inverting the vial according to a specified inversion protocol.

20. The method of claim 19, wherein, according to the inversion protocol, the agitating comprises performing a specified number of cycles, each cycle comprising:
  holding the vial in a first configuration;
  inverting the vial approximately 180 degrees into a second configuration;
  pausing movement of the vial for a known amount of time; and
  returning the vial to the first configuration.

21. The method of claim 19, wherein according to the inversion protocol the inverting lasts approximately one second, the pausing lasts approximately one half of a second, and the returning lasts approximately one second.

\* \* \* \* \*